(12) United States Patent
Steinberg et al.

(10) Patent No.: US 9,332,755 B2
(45) Date of Patent: May 10, 2016

(54) COVALENTLY ATTACHED ANTIMICROBIAL POLYMERS

(75) Inventors: Thorsten Steinberg, Mannheim (DE); Karen Lienkamp, Freiburg (DE); Pascal Tomakidi, Freiburg (DE); Ali Al-Ahmad, Freiburg (DE)

(73) Assignees: UNIVERSITAETSKLINIKUM FREIBURG, Freiburg (DE); ALBERT-LUDWIGS-UNIVERSITAET FREIBURG, Freiburg (DE)

( * ) Notice: Subject to any disclaimer, the term of this patent is extended or adjusted under 35 U.S.C. 154(b) by 231 days.

(21) Appl. No.: 13/997,444

(22) PCT Filed: Dec. 22, 2011

(86) PCT No.: PCT/EP2011/073786
§ 371 (c)(1),
(2), (4) Date: Sep. 5, 2013

(87) PCT Pub. No.: WO2012/089617
PCT Pub. Date: Jul. 5, 2012

(65) Prior Publication Data
US 2013/0338326 A1    Dec. 19, 2013

(30) Foreign Application Priority Data
Dec. 30, 2010 (EP) .................................... 10016218

(51) Int. Cl.
*A01N 43/08* (2006.01)
*A01N 25/10* (2006.01)
*C08F 8/00* (2006.01)
*C08F 291/18* (2006.01)
*C08F 292/00* (2006.01)
*A01N 25/34* (2006.01)

(52) U.S. Cl.
CPC .............. *A01N 43/08* (2013.01); *A01N 25/10* (2013.01); *A01N 25/34* (2013.01); *C08F 8/00* (2013.01); *C08F 291/18* (2013.01); *C08F 292/00* (2013.01)

(58) Field of Classification Search
CPC ....... A01N 25/10; A01N 25/34; A01N 43/08; C08F 291/19; C08F 292/00; C08F 8/00
USPC .................................................. 526/266, 268
See application file for complete search history.

(56) References Cited

U.S. PATENT DOCUMENTS

2006/0115448 A1 * 6/2006 Tew et al. .................... 424/78.3
2008/0251460 A1   10/2008 Gstrein et al.
2010/0317870 A1 * 12/2010 Tew et al. ..................... 548/453

OTHER PUBLICATIONS

International Search Report dated Apr. 12, 2012 corresponding to International Patent Application No. PCT/EP2011/073786.
International Preliminary Report on Patentability application No. PCT/EP2011/073786 dated Jul. 11, 2013.

* cited by examiner

*Primary Examiner* — Ling Choi
*Assistant Examiner* — Chun-Cheng Wang
(74) *Attorney, Agent, or Firm* — Squire Patton Boggs (US) LLP

(57) ABSTRACT

The present invention relates to substrates comprising covalently attached antimicrobial polymers, which act as synthetic mimics of antimicrobial peptides (SMAMPs) and are preferably obtained by ring opening metathesis polymerization (ROMP). The inventive antimicrobial polymers exhibit a molecular weight of more than 100,000 g mol$^{-1}$ and are preferably covalently attached to the surface of a substrate, e.g. an implant, a medical device, medical equipment or a (tissue-supporting) biomaterial, etc. Covalent bonding may be carried out using a photoreactive crosslinker but also by "grafting onto" or "grafting from". The present invention is also directed to uses of the inventive antimicrobial polymers as defined herein, e.g. for antimicrobially coating a surface of such a substrate with a layer of the inventive antimicrobial polymer.

16 Claims, 3 Drawing Sheets

COVALENTLY ATTACHED ANTIMICROBIAL POLYMERS

Figure 1:
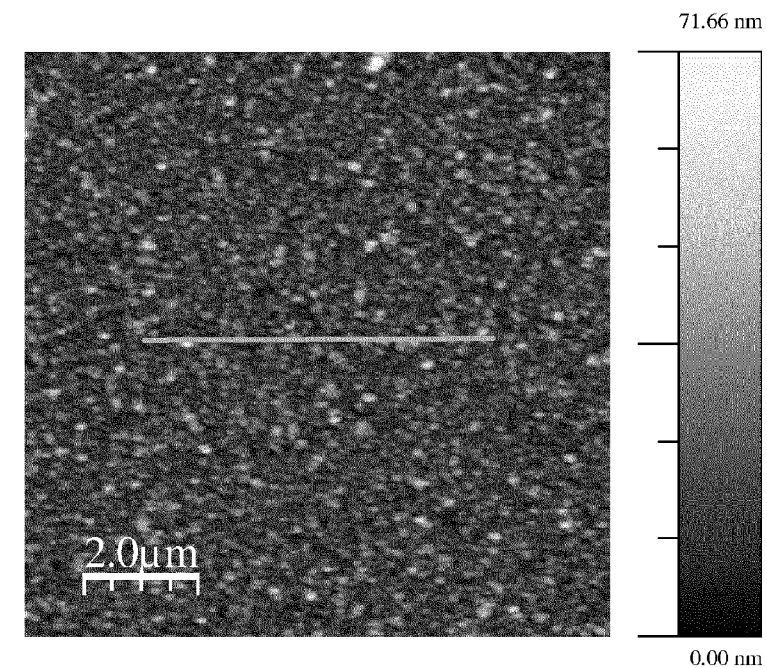
Figure 1:
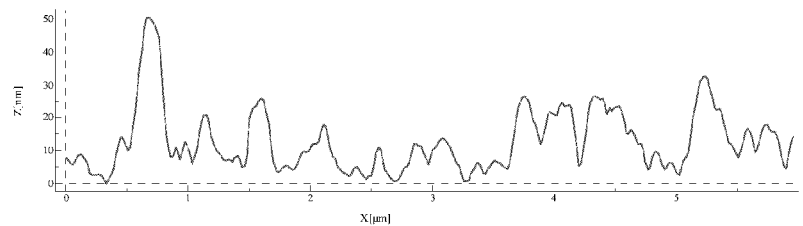

The present invention relates to substrates comprising covalently attached antimicrobial polymers, which act as synthetic mimics of antimicrobial peptides (SMAMPs) and are preferably obtained by ring opening metathesis polymerization (ROMP). The inventive antimicrobial polymers exhibit a molecular weight of more than 100,000 g mol$^{-1}$ and are preferably covalently attached to the surface of a substrate, e.g. an implant, a medical device, medical equipment or a (tissue-supporting) biomaterial, etc. Covalent bonding may be carried out using a photoreactive crosslinker but also by "grafting onto" or "grafting from". The present invention is also directed to uses of the inventive antimicrobial polymers as defined herein, e.g. for antimicrobially coating a surface of such a substrate with a layer of the inventive antimicrobial polymer.

A serious problem that can arise in the use of medical implants is infection by bacterial pathogens that cause infection and inflammation at the implantation site. This inflammation can inhibit healing at the site of implantation, or in a worse case, cause tissue destruction which can lead to the loss of the implant. Likewise, bacterial contamination of catheters and other medical devices can cause life-threatening infections even in healthy patients.

Despite measures directed at prevention, infections often occur due to colonization of the implant by bacteria. This process is exacerbated by the formation of a bacterial biofilm on the surface of the implant. The mature biofilm consists of various bacteria co-colonies surrounded by an extracellular matrix that offers protection to the bacteria, while also providing communication channels between individual bacteria. Once formed, the biofilm is extremely difficult to remove or to infiltrate with antibiotics; therefore prevention of colonization and/or (subsequent) formation of a biofilm is the means of choice. The requirement to prevent colonization and/or (subsequent) formation of a biofilm is an important issue in many clinical applications and surgical procedures. It is also of utmost importance in the case of soft-tissue implants, particularly in the field of periodontology, to prevent colonization and/or (subsequent) formation of a biofilm prior to implantation, as this may lead to unwanted inflammatory responses and a progressive destruction of the surrounding tissues.

In this context, many antimicrobial molecules and polymers have been developed, which may provide a good basis to prevent colonization and/or (subsequent) formation of a biofilm. In the last few years, significant progress has been made in the development of such antimicrobial molecules and polymers (see E.-R. Kenawy et al., Biomacromolecules 2007, 8, 1359-1384). Those materials are nonspecifically active against many pathogens including bacteria, viruses, and fungi, yet are also toxic for mammalian cells. Therefore, while highly efficient in their potential applications, those polymers cannot be used in settings in which there is intimate and long-term contact with eukaryotic cells, for example, in medical devices, implants, or wound dressings. Synthetic mimics of antimicrobial peptides (SMAMPs), on the other hand, are molecules that are specifically designed to only kill pathogens. SMAMPs were developed to emulate the properties of antimicrobial peptides (AMPs), which are natural molecules produced by many organisms as part of their innate immune system. These peptides have broad-spectrum antimicrobial activity, yet they are harmless to mammalian cells (see A. Kim A. Brodgen, Nat. Rev. Microbiol. 2005, 3, 238-250). Unlike traditional antibiotic drugs, they are not directed against a precise cellular receptor, but mostly act on the bacterial cell membrane (see A. Kim A. Brodgen, Nat. Rev. Microbiol. 2005, 3, 238-250 and L. Yang et al., J. Am. Chem. Soc. 2007, 129, 12141-12147). Thus, while resistance development against traditional antibiotics may involve only a few mutations of the receptor site upon exposure to sub-lethal drug doses, resistance to AMPs would require more complex changes including alterations of cell-membrane chemistry. Consequently, resistance build-up against AMPs is slower than against conventional antibiotics (see M. Zasloff, Nature 2002, 415, 389-395; G. G. Perron et al., Proc. R. Soc. B Biol. Sci. 2006, 273, 251-256). The combined properties of selectivity for pathogens over host cells and low-resistance potential have stimulated intense research in the field of AMPs and SMAMPs during the past few years. Due to their relative ease of synthesis, SMAMPs are promising candidates for both materials and chemotherapeutic applications; at the same time they appear to have the potential to play an important role in the containment of and contagion with MRSA and other multiple-resistant organisms. For example, a "first-in-man Phase I clinical safety study" was just recently reported, in which a SMAMP was used as the therapeutic agent for treatment of pan-staphylococcal infections (see e.g. http://www.polymedix.com).

As discussed in a review by Lienkamp and Tew (see Lienkamp and Tew, Chem. Eur. J. 2009, 15, 11784-11800), SMAMP design has evolved from structurally rigid, peptide-like molecules towards increasingly less-confined molecular architectures, some of which perform even better than their natural archetypes. Access to such synthetic SMAMPs may open up new applications, for example in the materials area, where bacterial infections from medical plastics are a current critical problem in our hospitals as discussed above. Synthetic polymers can be obtained easily and in large quantities while still presenting facial amphiphilicity and positive charge, the important features of AMPs. In this context, facially amphiphilic polymers typically contain a hydrophobic and a hydrophilic, charged group on the same repeat unit. Although there have been several recent reports of polymeric SMAMPs, their overall activities and selectivities remain far from optimal. In this context, DeGrado and coworkers reported SMAMPs based on poly(ammonium methylmethacrylate) salts copolymerized with poly(butylmethacrylate) to tune the amphiphilicity; Klajnert et al. produced dendritic SMAMPs; Liu et al. synthesized SMAMPs from poly(maleic acid) linked to peptide tetramers; Makovitzki et al. recently made SMAMPs based on lipopeptides; and Gellman and coworkers presented a poly(amide) based polymer with good activities (12.5 µg/mL against *E. coli* and 3.1 µg/mL against *S. aureus*) and selectivities up to 32 for bacterial over mammalian cells. (Kuroda et al., *Polymer Prepr.* 2004, 45, 610; Klajnert et al., *Int. J Pharm.* 2006, 309, 208; Liu et al., *J Med. Chem.* 2006, 49, 3436; Makovitzki et al., *Proc. Natl. Acad. Sci. USA* 2006, 103, 15997; Mowery et al. *J Am. Chem. Soc.* 2007, 129, 15474.) Tew and coworkers synthesized facially amphiphilic antibacterial polymers based on arylamides, urea, and poly(phenylene ethynylene) (see Tew et al., *Proc. Natl. Acad. Sci. USA* 2002, 99, 5110; Tang et al., *Chem. Commun.* 2005, 12, 1537; Amt et al., *J Am. Chem. Soc.* 2002, 124, 7664; and Amt et al., *Langmuir* 2003, 19, 2404).

Furthermore, Gstrein et al. (see US 2008/251460 A1) show biocidal polymers based on poly(norbornene) derivatives, which however, are statistic copolymers of a cationic and a hydrophobic repeat unit. Such statistic poly(norbornene) derivatives, even though showing biocidal activity, cannot be considered as selective for bacteria, as they cannot be fine tuned with regard to their local amphiphilicity. This, however, is crucial to obtain highly active polymers which target bacteria only and are benign to mammalian cells. This lack of selectivity is particularly due to the fact that the structure of the polymers in Gstrein et al. (see US 2008/251460 A1) cannot be precisely balanced on the repeat unit level, and does not contain facially amphiphilic repeat units. Antimicrobial polymers with high selectivity for bacteria, as also discussed in Lienkamp et al. (see Lienkamp et al., J. Am. Chem. Soc. 2008, 130, 9836; and Gabriel et al., Chem. Eur. J., 2009, 15, 433), however, typically require presence of facially amphiphilic repeat units, which is not the case in the static copolymers of Gstrein et al. The problem with statistic copolymers is that they contain runs of hydrophobic and hydrophilic repeat units. These hydrophobic "blobs" are then able to lyse the membrane of mammalian cells and thus cause cell toxicity. Gstrein et al. also use a mixture of endo- and exo-norbornene derivatives. These differ completely in their reaction kinetics. Thus, it is not possible to fine-tune the local structure of their reaction products.

SMAMPs based on poly(norbornene) derivatives were previously also described by Tew and Coughlin. In contrast to Gstrein et al. they reported polymers with facially amphiphilic repeat units that had tunable antimicrobial activity depending on a defined ratio of hydrophobic and hydrophilic moieties in the repeat unit. Their most selective polymer had a hundred times higher activity towards bacteria than against human red blood cells (Ilker et al., J Am. Chem. Soc. 2004, 126, 15870). They also very recently reported poly(norbornenes) with quaternary pyridinium groups (selectivities up to 20 against *E. coli*) (Eren et al., *Macromal. Chem. Phys.* 2008, 209, 516-524). These previously reported poly(norbornene) based SMAMPs suffered from the fact that each polymer required extensive synthetic effort to tune the amphiphilicity of the repeat units.

Notably, many publications also report a dependency of antimicrobial activity of AMPs and SMAMPs on molecular weight. In this context, the prior art shows molecular weight ranges of from a few hundred g mol$^{-1}$ to about 50,000 g mol$^{-1}$ and in any case below 100,000 g mol$^{-1}$ (see also Tew et al., US 2010/317870 A1). Lienkamp and Tew (2009, supra) even contend that previously presented data all referred to samples with a molecular weight of roughly 3,000 g mol$^{-1}$, although most of the studies mentioned therein (and above) investigated two or more compounds with different molecular weights for each polymer type. Lienkamp and Tew (2009, supra) also discuss how molecular weight in the known ranges affects SMAMP properties. For example, Lienkamp and Tew (2009, supra) found with respect for higher molecular weight ester-based polymers (series 2 in FIG. 4, $M_n$ 10,000 g mol$^{-1}$, biological data in FIG. 12 b) that these polymers were generally less active against *E. coli* when compared to their $M_n$ 3,000 g mol$^{-1}$ analogues, with the exception of a 10,000 g mol$^{-1}$ amine-propyl homopolymer. This amine-propyl homopolymer was surprisingly active against *E. coli*, More notably, the tested higher molecular weight polymers were all inactive against *S. aureus* (see also K. Lienkamp et al., J. Am. Chem. Soc. 2008, 130, 9836-9843). Similarly, diamine homopolymers with TFA counterions showed a systematic decrease in activity against *S. aureus* with increasing molecular weight, together with inactivity against *E. coli* at all molecular weights. This finding, additional to further observations, led to the hypothesis that, at higher molecular weights, these particular polymers get stuck in the peptidoglycan layer of Gram-positive bacteria. Similarly, Lienkamp et al., (Chem. Eur. J. 2009, 15, 11715-11722) showed that polymers of 3,000 g mol$^{-1}$, which have been shown to be inactive against *E. coli* but show a very good antimicrobial activity against *S. aureus*, loose their antimicrobial activity upon increasing the molecular weight. Interestingly, the hemolytic activity $HC_{50}$ was about the same for all molecular weights of these polymers.

Consequently, even though amphiphilic molecules have been discussed to be a promising basis for the development of future antimicrobial compounds, it appears to be very difficult to draw general conclusions concerning the dependency of biological activity on specific molecular structure and molecular weight. In most cases, in particular for antimicrobial polymers in solution, the general rule seems to hold that, when the molecular weight is above a certain threshold value, the polymers become inactive. Below this threshold, however, it does not appear to be possible to predict which molecular weight and which specific amphiphilic structure will give the best activities and selectivities, as this strongly depends on the overall hydrophobicity of the particular polymer studied.

Additional to the above, further requirements have to be fulfilled. Antimicrobial molecules and polymers are typically used in liquid or semi-liquid compositions, e.g. antimicrobial solutions, disinfectants, soaps, etc. but also may be used for the preparation of antimicrobial surfaces. In this context, different approaches can be seen in the prior art for the preparation of such antimicrobial surfaces.

According to one approach, such antimicrobial molecules and polymers may be applied to a surface in form of a coating (see e.g. U.S. Pat. No. 5,853,745). Such coatings may be placed on the surface of many implant materials and may also serve a number of functions, including antimicrobial activity. Advantageously, such coatings can perform as simple protective barriers, or can act multifunctionally as a protective barrier in combination with containing and releasing antimicrobial agents or antibiotics. Additionally, they can function to reduce or eliminate the formation of biofilms on the surface of the implant device. Unfortunately, these presently available coatings also demonstrate a number of serious inadequacies. Firstly, coatings such as those presented in U.S. Pat. No. 5,853,745 function as a protective film while incorporating antimicrobial/antibiotic compounds. This system relies on the leaching of antimicrobials/antibiotics out of a double coated system. Commonly, such systems result in a burst release type administration of active compounds followed by a progressive decline in concentration, concomitant with a reduction in efficacy. This non-linear time-dose relation may then lead to bacteria being exposed to sub-lethal doses of antibiotics, which may cause further development of resistant bacterial strains.

Another strategy may be the attachment of antimicrobial compounds such as the antibiotic compound Vancomycin to a surface. In US 2007/0107707 the antibiotic compound Vancomycin was attached to a polyacrylate polymer via PEG, while the polyacrylate polymer was itself attached to the surface of the material. This approach, although preventing a leaching out of the antimicrobial compounds, is only effective against specific organisms and may lead to the formation of resistance in some bacteria.

Other systems capable of antimicrobial action are those that apply the action of antimicrobial peptides or antimicrobial peptoids, as described in US Patent US 2009/0155335 and US 2010/0028719, respectively. The anti-microbial peptide system resulted in the production of surfaces that were shown to be resistant to bacterial adhesion for 28 days. Non-peptide systems are also described in US 2009/0155335, including zwitterionic surfaces produced from the attachment of carboxybetaine polymers. Concepts outlined in this patent, however, do not provide for a complete coverage of the implant surface and only allow antimicrobial action within a very short time limit.

One alternative to these problems may be the binding of antimicrobial molecules and polymers as discussed initially to a specific surface to prevent leaching of the antimicrobial coating. However, such a binding often goes along with a dramatic loss of activity of these antimicrobial molecules and polymers and many of such antimicrobial molecules and polymers have only been proven to be effective in solution.

In other cases, polymers were used as antimicrobial coatings although these polymers have been proven to be toxic in solution, or despite the fact that a correlation between solution and surface activity has not been investigated. As an example, US 2010/136072 (Klibanov and colleagues) shows hydrophobic polymeric coatings from poly(vinylpyridine polymers), which can be non-covalently applied to solid surfaces. However, these polymers in US 2010/136072 are biocidal, not only virucidal and bactericidal, i.e. they show no cell selectivity and thus also act against mammalian cells.

Bearing in mind all these difficulties, it is the object of the present invention to provide more adaptable antimicrobial molecules and polymers such as SMAMPs, which exhibit sufficient antimicrobial activity when covalently bound to a surface, e.g. an implant, but also allow for control of their antimicrobial properties such that they target only certain bacteria. Advantageously, such antimicrobial molecules and polymers are easy to apply to a surface, such as an implant and do not leach out but provide a long term effect to the coated surface. Likewise, such antimicrobial molecules and polymers also satisfy industrial requirements and may be produced in a cost-efficient manner.

The underlying problem is solved by novel and inventive antimicrobial polymers of any of formulae (I), (I') and (I") as defined herein as well as by co-polymers and blends thereof, which may be covalently bound to a surface of a substrate, e.g., an implant, a medical device or medical equipment, etc. and by such a surface or substrate and uses thereof. These inventive antimicrobial polymers are synthetic mimics of antimicrobial peptides (SMAMPs) and exhibit a molecular weight of more than 100,000 g mol$^{-1}$. Advantageously, such inventive SMAMPs, exhibiting a molecular weight of more than 100,000 g mol$^{-1}$, can be attached covalently to a surface in an efficient manner without impairing their antimicrobial activity. Furthermore, the present synthetic methods allow for a better control over the target molecular weight and polydispersity of the synthesized polymers, in particular providing polymers having a defined molecular weight of more than 100,000 g mol$^{-1}$ and a defined preferably linear structure. Control of target molecular weight and polydispersity is crucial, as molecular weights of more than 100,000 g mol$^{-1}$ are necessarily required to effectively link the inventive antimicrobial polymers to a surface using UV-crosslinking. This is in part due to the statistical nature of UV-crosslinking, where a minimum overall chain length is typically required to effectively bind the inventive antimicrobial polymer(s) to a surface as described herein, and to obtain full surface coverage. Unlike in previously reported cases on polymers without double bonds (see e.g. Prucker et al., J. Am. Chem. Soc. 1999, 121, 8766-8770), where the maximum surface film thickness reached a plateau after a certain time of UV exposure, and film thicknesses of only few nm were obtained, a prolonged exposure of the inventive antimicrobial polymers can provide a film thicknesses of up to 50 nm for a 100,000 g mol$^{-1}$ polymer, presumably by interaction with the poly(norbornene) double bonds.

Is has been previously shown by Prucker et al. (J. Am. Chem. Soc. 1999, 121, 8766) for polystyrene, a molecular weight of 50 000 g/mol is necessary to achieve complete coverage of a surface using the benzophenone method. For the inventively used polynorbornene polymers, the present inventors surprisingly found that a molecular weight of higher than 100,000 g/mol and even more preferably of higher than 250 000 g/mol is particularly advantageous to obtain a film that is covalently attached to the surface.

Besides photo-crosslinking reactions, the inventive antimicrobial polymers can be attached to the surface via "grafting onto" or via "grafting from" techniques. This means, that the inventive antimicrobial polymers are preferably polymerized and end-functionalized prior to covalent attachment to a surface as defined herein ("grafting onto"), or are polymerized in situ by an initiator that is covalently attached to the surface to obtain the covalently attached antimicrobial polymer ("grafting from"). The inventive antimicrobial polymers were designed by the present inventors through advanced polymer design and synthesis methods. In particular, for example, a ring opening metathesis polymerization (ROMP) platform was utilized that allows synthesis of both low and high molecular weight SMAMPs. These SMAMPs employ a minimum number of norbornene-based building blocks and/or enable easy and independent variation of hydrophobic and hydrophilic groups in the repeat units and/or along the polymeric backbone. This allows fine-tuning and selecting desirable properties (e.g., antimicrobial activity and cell selectivity) of these polymers.

Particularly, the underlying problem is solved according to a first embodiment by an antimicrobial polymer comprising as a repeat unit a structure according to formula (I):

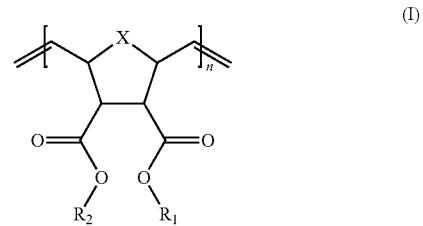

wherein preferably one of moieties $R_1$ and $R_2$ comprises a hydrophobic group and the other one of moieties $R_1$ and $R_2$ comprises a hydrophilic group, i.e. either $R_1$ represents a hydrophilic group and $R_2$ represents a hydrophobic group, or $R_1$ represents a hydrophobic group and $R_2$ represents a hydrophilic group, wherein X is O, S, N—R, P—R, or $CR_3R_4$, wherein $R_3$ and $R_4$ are preferably independently from each other selected from a hydrogen or a $C_1$-$C_{12}$ alkyl or alkoxy group, and wherein n is an integer preferably selected from about 150 to about 2500, preferably from about 250 to about 2500, for example from about 250 to about 750, from about 500 to about 1000, from about 750 to about 1250, from about 1000 to about 1500, from about 1250 to about 1700, from about 1500 to about 2000, from about 1750 to about 2250, or from about 2000 to about 2000, or from about 250 to about 1500 to about, from about 1000 to about 2500; etc.

The inventive antimicrobial polymer comprising as a repeat unit a structure according to formula (I) preferably comprises a molecular weight of more than 100,000 g mol$^{-1}$, preferably a molecular weight of at least 150,000 g mol$^{-1}$, a molecular weight of at least 200,000 g mol$^{-1}$, a molecular weight of at least 300,000 g mol$^{-1}$, or a molecular weight of at least 400,000 g mol$^{-1}$, more preferably the inventive antimicrobial polymer comprises a molecular weight in a range of about 100,000 g mol$^{-1}$ to about 1,000,000 g mol$^{-1}$, of about 150,000 g mol$^{-1}$ to about 1,000,000 g mol$^{-1}$, of about 200,000 g mol$^{-1}$ to about 1,000,000 g mol$^{-1}$, of about 300,000 g mol$^{-1}$ to about 1,000,000 g mol$^{-1}$, of about 400,000 g mol$^{-1}$ to about 1,000,000 g mol$^{-1}$, of about 150,000 g mol$^{-1}$ to about 900,000 g mol$^{-1}$, of about 200,000 g to about 800,000 g mol$^{-1}$, of about 300,000 g mol$^{-1}$ to about 700,000 g mol$^{-1}$, e.g. about 100,000 g mol$^{-1}$, about 150,000 g mol$^{-1}$, about 200,000 g mol$^{-1}$, about 300,000 g about 400,000 g mol$^{-1}$, about 500,000 g mol$^{-1}$, about 600,000 g mol$^{-1}$, about 700,000 g mol$^{-1}$, about 800,000 g mol$^{-1}$, about 900,000 g mol$^{-1}$, about 1,000,000 g mol$^{-1}$, or even more or may comprises a range formed by any of two of the above values.

In the context of the present invention, preferably in the context of an inventive antimicrobial polymer, the terms "hydrophobic group" or "hydrophobic moiety", as used herein, preferably refer to a group having a property such that an affinity of the (hydrophobic) group for water is low (e.g. being non-polar). Non-limiting examples of hydrophobic groups or moieties as used according to the present invention may comprise or consist of linear, branched, cyclic, substituted, unsubstituted, saturated, partially saturated and/or unsaturated compounds having 1 to 30 or more carbon atoms ($C_1$-$C_{30}$), preferably selected from ($C_1$-$C_{30}$) alkyl, alkenyl, alkynyl, aryl heteroalkyl, heteroalkenyl, heteroalkynyl, heteroaryl, heteroarylalkyl, cycloalkyl, cycloalkenyl, cycloalkynyl, heterocycloalkyl, or heterocycloalkenyl-groups, more preferably selected from linear, branched, cyclic, substituted and unsubstituted, saturated, partially saturated and/or unsaturated ($C_1$-$C_{30}$) alkyl, ($C_1$-$C_{30}$) alkenyl, ($C_1$-$C_{30}$) alkynyl, or ($C_1$-$C_{30}$) aryl groups, ($C_1$-$C_{30}$) heteroalkyl, ($C_1$-$C_{30}$) heteroalkenyl, ($C_1$-$C_{30}$) heteroalkynyl, ($C_1$-$C_{30}$) heteroaryl, or ($C_1$-$C_{30}$) heteroarylalkyl groups, or from linear, branched, cyclic, substituted, unsubstituted, saturated, partially saturated and/or unsaturated ($C_1$-$C_{30}$) cycloalkyl, ($C_1$-$C_{30}$) cycloalkenyl, ($C_1$-$C_{30}$) cycloalkynyl, ($C_1$-$C_{30}$) heterocycloalkyl, and ($C_1$-$C_{30}$) heterocycloalkenyl-groups, preferably having 1, 2, 3, 4, 1 to 3, 1 to 4, or even more rings. A hydrophobic group as defined herein may additionally contain some hydrophilic groups or substituents insofar as the hydrophobic character of the hydrophobic group is not outweighed. In further variations, a hydrophobic group as defined according to the present invention may include substituted silicon atoms and/or fluorine atoms. The hydrophobic moieties may be linear, branched, or cyclic.

In the context of the present invention, a $C_1$-$C_{30}$ group as defined above, e.g. any of the above defined ($C_1$-$C_{30}$) alkyl, alkenyl, alkynyl, aryl heteroalkyl, heteroalkenyl, heteroalkynyl, heteroaryl, heteroarylalkyl, cycloalkyl, cycloalkenyl, cycloalkynyl, heterocycloalkyl, or heterocycloalkenyl groups, may preferably include or be selected from a $C_1$-$C_{30}$, $C_1$-$C_{25}$, $C_1$-$C_{20}$, $C_1$-$C_{15}$, $C_1$-$C_{12}$, $C_1$-$C_6$, $C_6$-$C_{30}$, $C_{12}$-$C_{30}$, $C_{13}$-$C_{30}$, $C_{15}$-$C_{30}$, $C_{20}$-$C_{30}$ or a $C_{25}$-$C_{30}$ alkyl, alkenyl, alkynyl, aryl heteroalkyl, heteroalkenyl, heteroalkynyl, heteroaryl, heteroarylalkyl, cycloalkyl, cycloalkenyl, cycloalkynyl, heterocycloalkyl, or heterocycloalkenyl group, a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, or $C_{30}$ alkyl, alkenyl, alkynyl, aryl heteroalkyl, heteroalkenyl, heteroalkynyl, heteroaryl, heteroarylalkyl, cycloalkyl, cycloalkenyl, cycloalkynyl, heterocycloalkyl, or heterocycloalkenyl group, or an alkyl, alkenyl, alkynyl, aryl heteroalkyl, heteroalkenyl, heteroalkynyl, heteroaryl, heteroarylalkyl, cycloalkyl, cycloalkenyl, cycloalkynyl, heterocycloalkyl, or heterocycloalkenyl group selected from any range formed by any of two of the above values.

According to one exemplary aspect a $C_1$-$C_{12}$ alkyl, alkenyl, alkynyl, aryl heteroalkyl, heteroalkenyl, heteroalkynyl, heteroaryl, heteroarylalkyl, cycloalkyl, cycloalkenyl, cycloalkynyl, heterocycloalkyl, or heterocycloalkenyl group may preferably include or be selected from a $C_1$-$C_{12}$, $C_2$-$C_{12}$, $C_3$-$C_{12}$, $C_4$-$C_{12}$, $C_5$-$C_{12}$, $C_6$-$C_{12}$, $C_7$-$C_{12}$, $C_8$-$C_{12}$, $C_9$-$C_{12}$, $C_{10}$-$C_{12}$, $C_{11}$-$C_{12}$, $C_1$-$C_{11}$, $C_1$-$C_{10}$, $C_1$-$C_9$, $C_1$-$C_8$, $C_1$-$C_7$, $C_1$-$C_6$, $C_1$-$C_5$, $C_1$-$C_4$, $C_1$-$C_3$, or a $C_1$-$C_2$ alkyl, alkenyl, alkynyl, aryl heteroalkyl, heteroalkenyl, heteroalkynyl, heteroaryl, heteroarylalkyl, cycloalkyl, cycloalkenyl, cycloalkynyl, heterocycloalkyl, or heterocycloalkenyl group, or may be selected from a $C_1$, $C_2$, $C_3$, $C_4$, $C_5$, $C_6$, $C_7$, $C_8$, $C_9$, $C_{10}$, $C_{11}$, or a $C_{12}$ alkyl, alkenyl, alkynyl, aryl heteroalkyl, heteroalkenyl, heteroalkynyl, heteroaryl, heteroarylalkyl, cycloalkyl, cycloalkenyl, cycloalkynyl, heterocycloalkyl, or heterocycloalkenyl group, or from any range formed by any of two of the above values. Exemplary ($C_1$-$C_6$) alkyl groups include methyl, ethyl, n-propyl, isopropyl, n-butyl, isobutyl, pentyl, isopentyl, hexyl, etc. Of course, other ($C_1$-$C_6$) alkyl groups will be readily apparent to those of skill in the art given the benefit of the present disclosure. Exemplary ($C_1$-$C_6$) alkenyl groups include ethenyl, 1-propenyl, 1-butenyl, 2-butenyl, 1,3-butadienyl, 1-penten, 2-penten, 2-methyl-3-buten, 2-methyl-3-penten, 3-methyl-2-penten, 4-methyl-3-penten, etc. Likewise, other ($C_1$-$C_6$) alkenyl groups will be readily apparent to those of skill in the art given the benefit of the present disclosure. The same applies to alkynyl, aryl heteroalkyl, heteroalkenyl, heteroalkynyl, heteroaryl, heteroarylalkyl, cycloalkyl, cycloalkenyl, cycloalkynyl, heterocycloalkyl, or heterocycloalkenyl groups as defined above.

According to a specific aspect, the hydrophobic group of $R_1$ or $R_2$ of the inventive antimicrobial polymer according to formula (I) may be selected from a $C_1$-$C_{12}$ or $C_1$-$C_6$ alkyl, alkenyl, alkynyl, aryl heteroalkyl, heteroalkenyl, heteroalkynyl, heteroaryl, heteroarylalkyl, cycloalkyl, cycloalkenyl, cycloalkynyl, heterocycloalkyl, or heterocycloalkenyl group as defined above, preferably from a linear or branched substituted or unsubstituted $C_1$-$C_{12}$ alkyl group as defined above, e.g., a linear or branched substituted or unsubstituted $C_1$-$C_{12}$ alkyl group or $C_1$-$C_6$ alkyl group.

Furthermore, the terms "hydrophilic group" or "hydrophilic moiety" as used herein in the inventive antimicrobial polymer according to formula (I), preferably refer to a group having a property such that an affinity of the group for water is high (e.g., high polarity). Non-limiting examples of hydrophilic groups or moieties include hydroxyl, methoxy, carboxylic acids and ions and salts thereof, amides, amino, cyano, isocyano, nitrile, ammonium ions or salts, sulfonium ions or salts, phosphonium ions or salts, mono- and di-alkyl substituted amino groups, polyethylene glycols, glycosyl groups, sugars, epoxy groups, acrylates, sulfonamides, nitro, guanidinium, biguanidinum, aminate, acrylamide, pyridinium, piperidine, pyrazole, pyrol, imidazole, azirine, aziridine, diaziridine, azetidine, azete, diazetidine, azolidine, phospholane, phosphole, arsolane, arsole, imidazolidine, pyrazolidine, imidazolin, pyrazoline, oxazolidine, isoxazolidine, oxazole, oxazoline, isoxazole, isoxazoline, thiazolidin, isothiazolidin, thiazole, thiazolin, isothiazole, isothiazoline, triazole, dithiazole, furazan, oxadiazole, thiadiazole, tetrazole, piperazin, diazine, morpholin, oxazin, thiazin, triazin, tetrazine, zwitterions or amino acids, and combinations thereof, or from OP(O)(OCH$_2$CH$_2$N$^+$RRR)O$^-$, wherein each R is independently selected from H or an alkyl as defined herein. Further examples include poly(methylene) chains substituted with alcohol, carboxylate, acrylate, or methacrylate. Hydrophilic moieties may also include alkyl chains having internal amino or substituted amino groups, for example, internal —NH, —NC(O)R, or —NC(O)CH=CH$_2$-groups, wherein R is H or an alkyl as defined herein. Hydrophilic moieties may also include poly(caprolactone(s)), poly(caprolactone diol(s)), poly(acetic acid)(s), poly(vinyl acetates)(s), poly(2-vinyl pyridine)(s), cellulose ester(s), cellulose hydroxylether(s), poly(L-lysine hydrobromide)(s), poly(itaconic acid)(s), poly(maleic acid)(s), poly(styrenesulfonic acid)(s), poly(aniline)(s), or poly(vinyl phosphonic acid)(s), poly(zwitterions) or poly(aminoacids). A hydrophilic group may contain some hydrophobic groups or substituents insofar as the hydrophilic character of the group is not outweighed.

According to one specific aspect, the hydrophilic group of $R_1$ or $R_2$ of the inventive antimicrobial polymer according to formula (I) may include e.g. a group selected from ammonium ions, sulfonium ions, phosphonium ions, and mono- and di-alkyl substituted amino groups, preferably an $C_1$-$C_{12}$ alkyl as defined above, comprising a group selected from ammonium ions, sulfonium ions, phosphonium ions, and mono- and di-alkyl substituted amino groups.

According to one even more specific aspect, the hydrophobic group of $R_1$ or $R_2$ of the inventive antimicrobial polymer according to formula (I) may be selected from the group

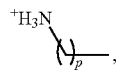

wherein p is an integer preferably selected from a range selected from 1-10, 1-9, 1-8, 1-7, 1-6, 1-5, 1-4, 1-3, 1-2, or preferably selected from a range selected from 1-10, 2-10, 3-10, 4-10, 5-10, 6-10, 7-10, 8-10, or 9-10, or preferably selected from 1, 2, 3, 4, 5, 6, 7, 8, 9, or 10 or preferably selected from any range formed by any of two of the above values.

According to a particularly specific aspect in the antimicrobial polymer according to formula (I) as defined above, X is O and $R_1$ is a linear or branched $C_1$-$C_{12}$ alkyl group as defined above, e.g., a linear or branched $C_1$-$C_6$ alkyl group as defined above; and $R_2$ is

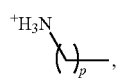

wherein p is an integer preferably selected from a range selected from 1-10, 1-9, 1-8, 1-7, 1-6, 1-5, 1-4, 1-3, 1-2, or preferably selected from a range selected from 1-10, 2-10, 3-10, 4-10, 5-10, 6-10, 7-10, 8-10, or 9-10, or preferably selected from 1, 2, 3, 4, 5, 6, 7, 8, 9, or 10 or preferably selected from any range formed by any of two of the above values.

According to an alternative specific aspect in the antimicrobial polymer according to formula (I) as defined above, X is $CR_3R_4$ as defined above, wherein $R_3$ and $R_4$ are preferably independently from each other selected from a hydrogen, or a $C_1$-$C_{12}$ alkyl or alkoxy group as defined above, most preferably a hydrogen; $R_1$ is a linear or branched $C_1$-$C_{12}$ alkyl group (e.g., a $C_1$-$C_6$ alkyl group); and $R_2$ is

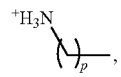

wherein p is an integer preferably selected from a range selected from 1-10, 1-9, 1-8, 1-7, 1-6, 1-5, 1-4, 1-3, 1-2, or preferably selected from a range selected from 1-10, 2-10, 3-10, 4-10, 5-10, 6-10, 7-10, 8-10, or 9-10, or preferably selected from 1, 2, 3, 4, 5, 6, 7, 8, 9, or 10 or preferably selected from any range formed by any of two of the above values.

According to particularly preferred aspect the antimicrobial polymer comprising as a repeat unit a structure according to formula (I) as defined above is an antimicrobial co-polymer comprising as repeat units a structure according to formula (I') and a further structure according to formula (I"):

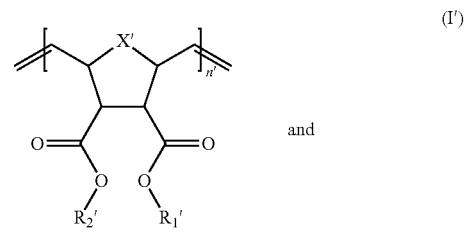

and

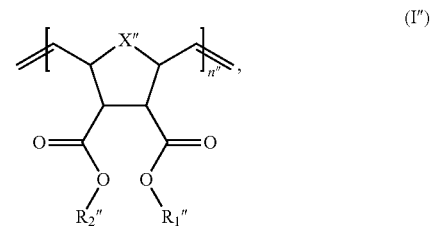

wherein each of X' and X" are preferably independent from each other as defined above for X in formula (I) and are the same or are not the same,
wherein each of $R_1$' and $R_1$" are preferably independent from each other as defined above for $R_1$ in formula (I) and are the same or are not the same, and
wherein each of $R_2$' and $R_2$" are preferably independent from each other as defined above for $R_2$ in formula (I) and are the same or are not the same, and
wherein each of integers n' and n" in formulae (I') and (I") may be defined as above for n in formula (I) and may be such that n'+n"=n.

Likewise, the inventive antimicrobial co-polymer comprising as repeat units a structure according to formula (I') and a further structure according to formula (I") comprises a molecular weight of more than 100,000 g mol$^{-1}$, preferably a molecular weight of at least 150,000 g mol$^{-1}$, a molecular weight of at least 200,000 g mol$^{-1}$, a molecular weight of at least 300,000 g mol$^{-1}$, or a molecular weight of at least 400,000 g mol$^{-1}$, more preferably the inventive antimicrobial polymer comprises a molecular weight in a range of about 100,000 g mol$^{-1}$ to about 1,000,000 g mol$^{-1}$, of about 150,000 g mol$^{-1}$ to about 1,000,000 g mol$^{-1}$, of about 200,000 g mol$^{-1}$ to about 1,000,000 g mol$^{-1}$, of about 300,000 g mol$^{-1}$ to about 1,000,000 g mol$^{-1}$, of about 400,000 g mol$^{-1}$ to about 1,000,000 g mol$^{-1}$, of about 150,000 g mol$^{-1}$ to about 900,000 g mol$^{-1}$, of about 200,000 g mol$^{-1}$ to about 800,000 g mol$^{-1}$, of about 300,000 g mol$^{-1}$ to about 700,000 g mol$^{-1}$, e.g. about 100,000 g mol$^{-1}$, about 150,000 g mol$^{-1}$, about 200,000 g mol$^{-1}$, about 300,000 g mol$^{-1}$, about 400,000 g mol$^{-1}$, about 500,000 g mol$^{-1}$, about 600,000 g mol$^{-1}$, about 700,000 g mol$^{-1}$, about 800,000 g mol$^{-1}$, about 900,000 g mol$^{-1}$, about 1,000,000 g mol$^{-1}$, or even more or may comprises a range formed by any of two of the above values.

Preferably, each of $R_1'$ and $R_1''$ in formulae (I') and (I'') is a hydrophobic group and each of $R_2'$ and $R_2''$ is a hydrophilic group as defined above for $R_1$ or for $R_2$ in formula (I) and are preferably the same or are not the same. More preferably, either $R_1'$ and $R_1''$ are the same and $R_2'$ and $R_2''$ are not the same, or $R_1'$ and $R_1''$ are not the same and $R_2'$ and $R_2''$ are the same. Even more preferably, $R_1'$ and $R_1''$ are not the same and $R_2'$ and $R_2''$ are the same.

Nevertheless, according to a further particular example, either ($R_1'$ and $R_2'$) or ($R_1''$ and $R_2''$) may be both a hydrophobic or a hydrophilic group as defined above for $R_1$ or for $R_2$ in formula (I), preferably provided that not both of ($R_1'$ and $R_2'$) and ($R_1''$ and $R_2''$) represent a hydrophobic or a hydrophilic group.

Additionally X' and X'' in formulae (I') and (I'') may be the same or not the same. More preferably, X' and X'' are not the same.

According to a very specific aspect, each of X' and X'' in formulae (I') and (I'') is preferably independent from each other O, S, or $CR_3R_4$ as defined above, wherein $R_3$ and $R_4$ are preferably independently from each other selected from a hydrogen or a $C_1$-$C_{12}$ alkyl or alkoxy group as defined above, e.g., a $C_1$-$C_6$ alkyl or alkoxy group; each of $R_1'$ and $R_1''$ is preferably a hydrophobic group as defined above and each of $R_2'$ and $R_2''$ is preferably a hydrophilic group as defined above, provided that $R_1'$ and $R_1''$ are preferably not the same, $R_2'$ and $R_2''$ are preferably the same, or X' and X'' are preferably not the same; and each of n' and n'' is preferably an integer such that n'+n''=n.

In a further very specific aspect, each of $R_1'$ and $R_1''$ in formulae (I') and (I'') is preferably independent from each other a linear or branched $C_1$-$C_{12}$ alkyl group as defined above, e.g., a $C_1$-$C_6$ alkyl group; and each of $R_2'$ and $R_2''$ is preferably independent from each other

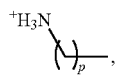

wherein p is an integer preferably selected from 1-10, 1-9, 1-8, 1-7, 1-6, 1-5, 1-4, 1-3, 1-2, or preferably selected from 1-10, 2-10, 3-10, 4-10, 5-10, 6-10, 7-10, 8-10, or 9-10, or preferably selected from 1, 2, 3, 4, 5, 6, 7, 8, 9, or 10 or preferably selected from any range formed by any of two of the above values.

In another very specific aspect, each of X' and X'' in formulae (I') and (I'') is O. In some other very specific aspects, each of X' and X'' is independently $CR_3R_4$, wherein $R_3$ and $R_4$ are preferably as defined above. In some further specific aspects, one of X' and X'' in formulae (I') and (I'') is O and the other is $CR_3R_4$, wherein $R_3$ and $R_4$ are preferably as defined above.

In the context of the present invention the inventive antimicrobial polymers, which are defined by their repeat units according to any of formulae (I), (I') and (I''), and in particular their repeat units may exist in particular geometric or stereoisomeric forms. The present invention contemplates all such compounds, including exo- and endo-isomers, cis- and trans-isomers, R- and S-enantiomers, diastereomers, (D)-isomers, (L)-isomers, the racemic mixtures thereof, and other mixtures thereof, as falling within the scope of the present invention. Additional asymmetric carbon atoms may be present in a substituent such as an alkyl group. All such isomers, as well as mixtures thereof, are intended to be included in this invention.

Furthermore, it will be appreciated that the inventive antimicrobial polymers, which are defined by their repeat units according to any of formulae (I), (I') and (I''), and in particular their repeat units may be further substituted with any number of substituents or functional moieties, if necessary. E.g. the inventive antimicrobial polymers may be modified to comprise hydrophobic and hydrophilic groups attached to the polymeric backbone such that, within a structural repeat unit, hydrophobic and/or hydrophilic groups are attached to the polymeric backbone at adjacent atoms, e.g. via ester linkages.

Given the benefit of this disclosure, one of ordinary skill in the art will also appreciate that synthetic methods, as described herein, utilize a variety of protecting groups and monomers as well as polymers as defined herein, which therefore may be modified and probably also provided with such protecting groups. By the term "protecting group", as used herein, it is meant that a particular functional moiety, e.g., OH, SH, or $NH_2$, is temporarily blocked so that a reaction can be carried out selectively at another reactive site in a multifunctional compound. In preferred embodiments, a protecting group reacts selectively in good yield to give a protected substrate that is stable to the projected reactions; the protecting group should be selectively removable in good yield by readily available, preferably non-toxic reagents that do not attack the other functional groups; the protecting group forms an easily separable derivative (more preferably without the generation of new stereogenic centers); and the protecting group has a minimum of additional functionality to avoid further sites of reaction. Preferably, oxygen, sulfur, nitrogen, and carbon protecting groups may be utilized for this purpose. Examples of a variety of protecting groups can be found in *Protective Groups in Organic Synthesis*, Third Ed. Greene, T. W. and Wuts, P. G., Eds., lohn Wiley & Sons, New York: 1999. Such protecting groups may comprise e.g. a ten-Butyloxycarbonyl (BOG) group, a carbobenzyloxy (Cbz) group, a p-Methoxybenzyl carbonyl (Moz or MeOZ) group, a 9-Fluorenylmethyloxycarbonyl (FMOC) group, etc. Amines, which are reacted with a protection group prior to their use in the inventive synthesis method, may comprise e.g. a tert-butyl carbamate (NHBoc) (see Slugovc et al., *Macromol. Rapid Commun.* 2004, 25, 1283), etc.

The inventive antimicrobial polymers, which are defined by their repeat units according to any of formulae (I), (I') and (I''), may be prepared according to any chemical synthesis that may be suitable for a skilled person. More preferably, the present invention utilizes a novel and unique approach for preparation of the inventive antimicrobial polymers based on a ring-opening metathesis polymerization (ROMP) platform that (i) uses a minimum number of building blocks and (ii) allows the easy and independent variation of the hydrophobic and hydrophilic residues on the respective repeat units. In this approach, hydrophilic and hydrophobic components are preferably attached to a polymerizable norbornene or oxanorbornene group, or any derivative, and can be varied independently.

Accordingly, inventive antimicrobial polymers, which are defined by their repeat units according to any of formulae (I), (I') and (I''), may be obtained by using the inventive ring-opening metathesis polymerization (ROMP) method as defined below. Preferably, such a method comprises preparation of the monomeric units in a first step and polymerization of the monomeric units in a second step.

According to an (optional) first step of the inventive method for preparing the inventive antimicrobial polymers the monomeric units of the inventive antimicrobial polymers according to any of formulae (I), (I') and (I") may be prepared. More precisely, the (optional) first step of the inventive method may be carried out by utilizing an easy and modular synthetic pathway towards facially amphiphilic monomers via three substeps. In the first substep, preferably furan and maleic anhydride are mixed and undergo a Diels-Alder reaction, yielding exclusively the exo-adduct in accordance with the literature (see Mantovani et al., *J. Am. Chem. Soc.* 2005, 127, 2966). This facile substep provides a first reaction product containing a polymerizable oxanorbornene group and a cyclic anhydride that allows twofold and unsymmetrical functionalization. In a second substep the anhydride obtained by the first substep may then be ring-opened with an alcohol R—OH to introduce the desired hydrophobic moiety R, wherein residue R may be defined as indicated for any of the moieties $R_1$, $R_2$, $R_1'$, $R_2'$, $R_1''$ and $R_2''$ in any of formulae (I), (I') and (I"). This substep preferably yields a "half-monomer" (monoester) or, if different alcohols R—OH are used for ring-opening, even a series of half-monomers (monoesters) with the same or different hydrophobicities. This substep is particularly suitable to adapt the hydrophobic properties of the resulting polymer as necessary. All compounds obtained in the second substep may be crystallized and purified. In a third and preferably last substep, a designated hydrophilic group as defined above may be attached to the ring-opened half monomer. This substep is particularly suitable to adapt the hydrophilic properties of the resulting polymer as necessary. If amines are used as designated hydrophilic group in this third substep, such an amine may be provided when bound to a protecting group, e.g. as defined above, as ROMP usually does not tolerate the presence of unprotected amines due to their ligating properties. The half-monomers (monoesters) may be reacted, e.g. with the protected Boc-protected 2-amino ethanol by DCC coupling, yielding a masked amphiphilic monomer or even a series of masked amphiphilic monomers, if different alcohols R—OH were used for ring-opening. The compounds obtained in the last substep may be purified, e.g. via column chromatography, precipitation or recystallization to yield pure products.

Alternatively, second and third substeps may be interchanged to provide important key intermediates, which may be reacted to the monomers as defined according to any of formulae (I), (I') and (I") more efficiently. According to this alternative, the second substep, i.e. ring opening, may be carried out with a Boc protected amino alcohol. Preferably, ring opening may be carried out with a Boc-protected 2-amino ethanol, similar as shown in Scheme-2. Likewise, this alternative second substep yields a "half-monomer" (monoester) having a Boc-protected amino moiety, preferably representing the hydrophilic moiety as defined above. The product of this alternative second substep may be further reacted in an alternative third substep with a further alcohol R—OH to introduce the desired hydrophobic moiety R in an alternative third substep, wherein residue R may be defined as indicated for any of the moieties $R_1$, $R_2$, $R_1'$, $R_2'$, $R_1''$ and $R_2''$ in any of formulae (I), (I') and (I"). All compounds obtained in the alternative second and third substeps may be crystallized and purified as indicated above.

According to a specific aspect of the present invention, optional step 1 of the inventive method for preparing the inventive antimicrobial polymers the monomeric units of the inventive antimicrobial polymers according to any of formulae (I), (I') and (I") may be carried out as outlined below in Scheme-1 by mixing furan and maleic anhydride, e.g. in toluene, which undergo a Diels-Alder reaction, yielding exclusively the exo-adduct in accordance with the literature (Mantovani et al., *J Am. Chem. Soc.* 2005, 127, 2966). This substep 1 preferably provides compound 1 as illustrated in Scheme-1 shown in the following containing a polymerizable oxanorbornene group and a cyclic anhydride that allows twofold and unsymmetrical functionalization. The anhydride 1 is then preferably ring-opened in a substep 2 with an alcohol R—OH as defined above, preferably comprising as organic moieties a methyl (a), an ethyl (b), a propyl (c), a butyl (d) an isopentyl (e) or a hexyl (f). This substep 2 allows introducing the desired hydrophobic moiety R yielding a series of half-monomers 2, in particular 2a-f with different hydrophobicities. All compounds are crystallizable and may be purified easily. In a further substep 3, a designated cationic group is preferably attached. As ROMP usually does not tolerate the presence of unprotected amines due to their ligating properties, e.g. the desired hydrophilic group ($NH^{3+}$) may be introduced in its protected tert-butyl carbamate (NHBoc) form (Slugovc et al., *Macromol. Rapid Commun.* 2004, 25, 1283). The half-monomers 2a-f may be reacted with the Bac-protected 2-amino ethanol by DCC coupling, yielding a series of masked amphiphilic monomers 3a-f (see Scheme-1). This last substep may be subjected to purification by column chromatography to yield pure products.

Scheme-1: Monomer Synthesis. The hydrophobic cojmponent of the facially amphiphilic monomer is introduced in the second substep (R = methyl, ethyl, propyl, butyl, isopentyl or hexyl), and the protected hydrophilic moiety is attached in the last substep.

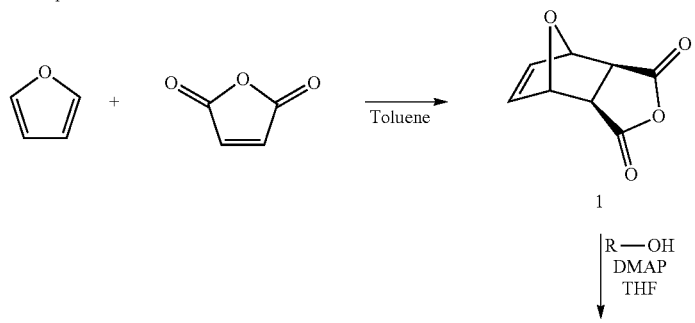

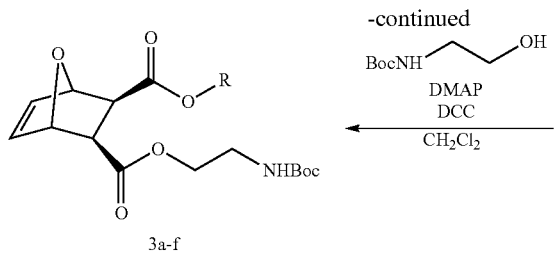
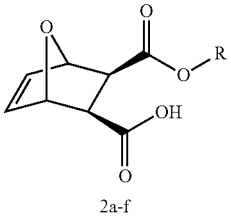

According to a particularly specific aspect, diamine monomers may be synthesized in accordance to the protocol as shown above by carrying out the ring opening metathesis in substep 2 and the reaction of the intermediate according to substep 3 with a hydrophilic component as defined above, more preferably with an amine component, by introducing e.g. the desired hydrophilic group ($NH^{3+}$) in its protected tert-butyl carbamate (NHBoc) form. This specific variant is illustrated in Scheme-2 below:

Scheme-2: Diamine monomer synthesis.

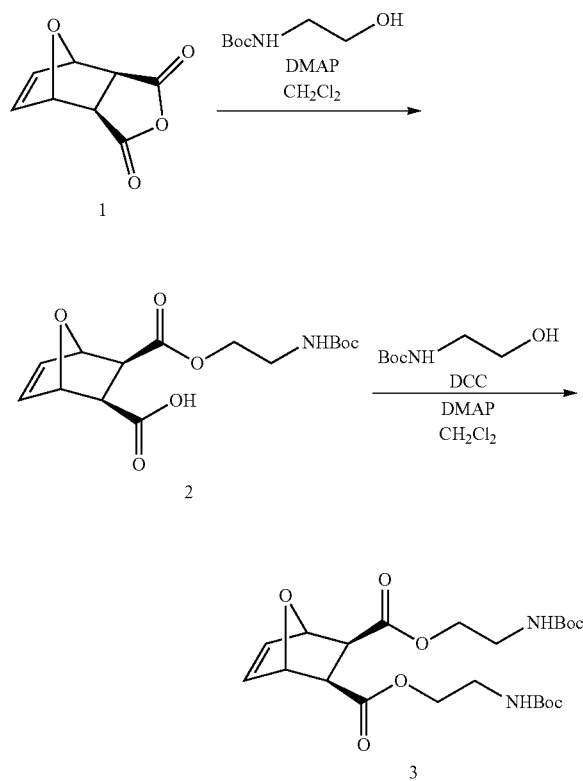

Such diamine monomers may also be used for producing co-polymers as defined above.

According to a second step of the inventive method for preparing the inventive antimicrobial polymers the monomeric subunits according to any of formulae (I), (I') and (I") may be subjected to a polymerization reaction. The polymerization of the monomers as obtained according to step a of the inventive method, preferably via substeps 1, 2 and 3 of the first step as discussed above, may be carried out using Grubbs catalyst, preferably the third generation Grubbs catalyst (Dichloro-di(3-bromopyridino)-N,N'-dimesitylenoimidazolino-Ru=CHPh (G3)) or a modified Grubbs catalyst G3' (Grubbs $3^{rd}$ generation catalyst with pyridine as ligands (G3') instead of the traditional G3 with 2-bromo pyridine ligands, see following formula)

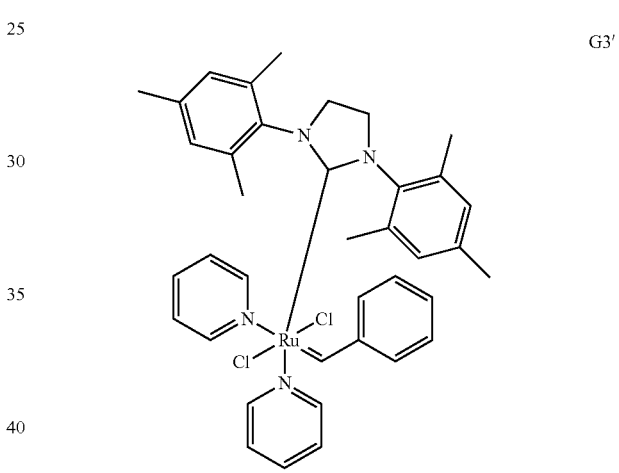

In this context, such a Grubbs catalyst (G3) as well as the modified third generation Grubbs catalyst (G3') may be prepared according to the procedure outlined by Grubbs and coworkers (see Love, J. A.; Morgan, J. P.; Trnka, T. M.; Grubbs, R. H. *Angew. Chem., Int. Ed.* 2002, 41, 4035). These catalysts are preferably fully soluble in the solvents used herein. Grubbs catalyst G3 or more preferably modified Grubbs catalyst G3', is preferably (fully) solubilized in an unpolar solvent, such as dichoromethane or THF. The mixtures are then preferably subjected to at least one, two or even three freeze-thaw cycles. The polymerization is started upon mixing the monomers and the catalyst and is carried on until specific termination of the polymerization reaction. The reaction is preferably carried out between about 3 and about 60 minutes, more preferably between about 3 and 40 about minutes, even more preferably between about 20 and 40 about minutes, e.g. in a time of about 30 minutes. Gelation of the polymer is also preferably avoided. Temperatures are usually in a range of between about 15° C. and about 30° C., preferably in a range of between about 20° C. and about 25° C., e.g. about room temperature.

Specific termination of the polymerization reaction is typically carried out using a terminating agent. Preferably, the "living" polymer (i.e. the inventive antimicrobial polymers with a chain-end containing a ruthenium species prior to termination of the reaction) is "end-capped" or quenched with the terminating agent and the polymerization is stopped quantitatively. Such a terminating agent may be selected from any terminating agent, which is suitable for a skilled person to terminate the polymerization reaction, e.g. from an ethyl vinyl ether or a 2-butene-1,4-diol derived terminating compound selected from a pentafluorophenylester or a pentafluorophenylether, e.g. terminating compound 1 (O1-[(Z)-4-[4-oxo-4-(2,3,4,5,6-pentafluorophenoxy)butanoyl]oxybut-2-enyl]O4-(2,3,4,5,6-pentafluorophenyl)butanedioate):

or terminating compound 2 ((2,3,4,5,6-pentafluorophenyl) 3-[(Z)-4-[3-oxo-3-(2,3,4,5,6-pentafluorophenoxy)propoxy]but-2-enoxy]propanoate):

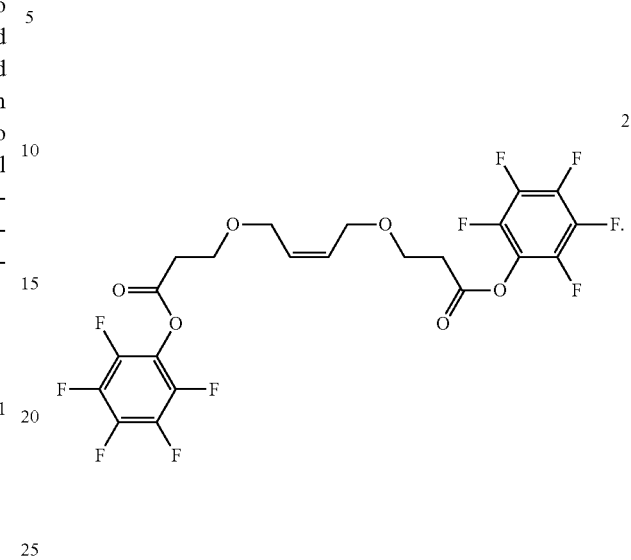

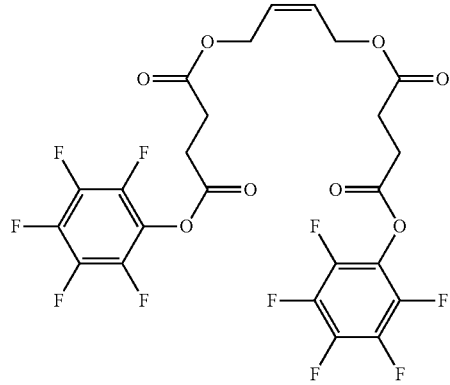

Such terminating agents 1 and 2 may also be used to end-functionalize the living polymers (i.e. the inventive antimicrobial polymers during the polymerization reaction prior to termination of the reaction) in such a way as to allow reacting of the end-functionalized polymers with any further compound and/or to allow binding of the end-functionalized polymers to a surface ("grafting onto"), etc. Termination of polymerization using the terminating agents 1 and 2 may be carried out generally as outlined below in Scheme-3:

Scheme-3: Termination of polymerization and end-functionalization of inventive living polymers with terminating agents 1 (pentafluoroallyl ester) and 2 (pentafluoroallyl ether);

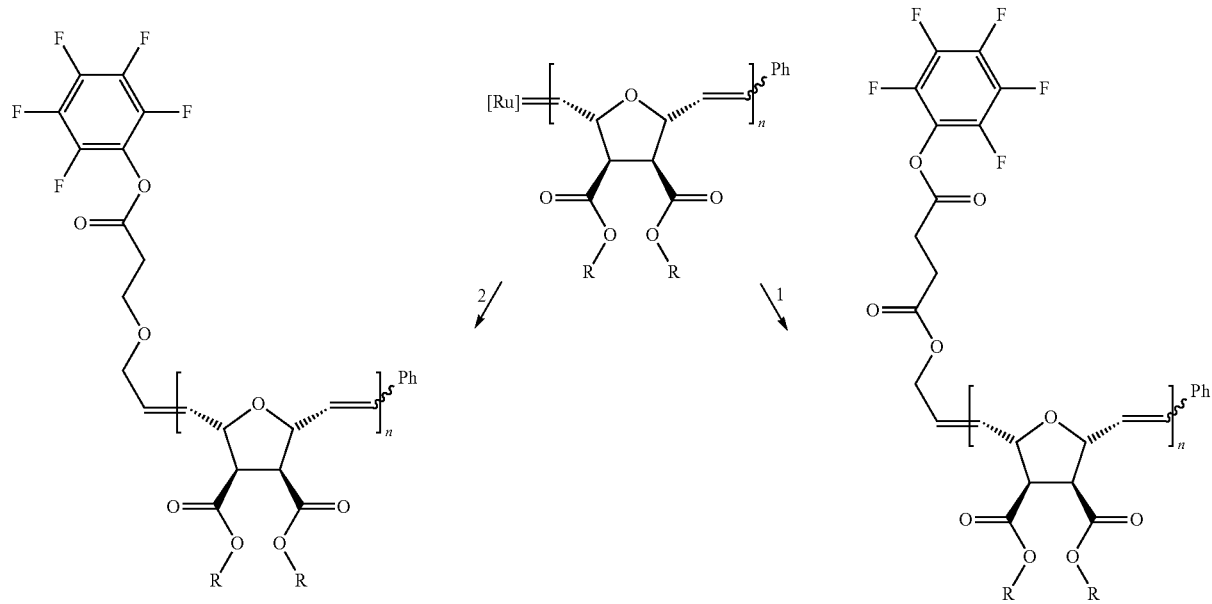

Termination of polymerization preferably yields precursors of the inventive antimicrobial polymers, more precisely end-capped or end-functionalized inventive antimicrobial polymers in their protected form, with molecular weights from 1,000 to 1,000,000 g mol$^{-1}$, preferably with molecular weights from 3,000 to 1,000,000 g mol$^{-1}$, more preferably with molecular weights of more than 100,000 g mol$^{-1}$. Any of these end-capped or end-functionalized polymers (either protected or deprotected) are also covered by the present invention (as precursors), preferably when covalently bound to a surface or a substrate as defined herein using grafting from as defined herein. The inventive facially amphiphilic SMAMPs may then be obtained via polymer analogous deprotection: For this purpose, the protecting group, e.g., a Boc protecting group, is typically removed, preferably with an acid, e.g. with trifluoroacetic acid or HCl. The success of the reaction and removing of the protecting group may be controlled by NMR, if the polymers are in solution. Depending on the alkyl residue, the resulting crude polymers are water-soluble or dispersible.

According to a specific aspect of the present invention, the second step of the inventive method for preparing the inventive antimicrobial polymers may be carried out as outlined below in Scheme-4. Specifically Grubbs 3$^{rd}$ generation catalyst with pyridine as ligands (G3') may be used instead of the traditional G3 with 2-bromo pyridine ligands. In a typical experiment, the monomers and the respective amount of catalyst G3 or G3', preferably G3', may be dissolved in dichloromethane and subjected to three freeze-thaw cycles. Preferably, the amounts of the monomers according to any of formulae (I), (I') and (I"), either the single monomers or a mixture thereof, may be about 250 to about 750 g mol$^{-1}$, more preferably about 400 to about 600 g mol$^{-1}$, e.g. about 500 g mol$^{-1}$. Preferably, the amount of the catalyst may be about 0.5 mg to 2 mg e.g. 1 mg. The monomers may then be added in one shot to the vigorously stirring catalyst solution, preferably at room temperature under argon. After about 20 to about 40 about minutes, e.g. after a time of about 30 minutes, the polymer chain reaction is preferably terminated by end-capping the living polymer with an excess of a terminating agent, e.g. ethylvinyl ether (1 mL). The solution may then be allowed to stir over night. After evaporation of the solvent and drying, an aliquot of each polymer may be taken for GPC and NMR analysis. The polymerization yields the precursor polymers 4a-f (endcapped and protected). The molecular weights may be determined by GPC analysis using polystyrene standards for calibration. A specific procedure for polymer synthesis is shown in Scheme-4.

Scheme-4: Polymer Synthesis. ROMP polymerization is followed by polymer analogous hydrolysis with an acid, such as trifluoroacetic acid, to yield the facially amphiphilic polymer. Likewise, this exemplary synthesis leads to the precursors of the inventive antimicrobial polymers with molecular weights from 1,000 to 1,000,000g mol$^{-1}$. The inventive antimicrobial polymers may then be obtained by deprotection subsequent to covalent binding on a surface or substrate as defined herein.

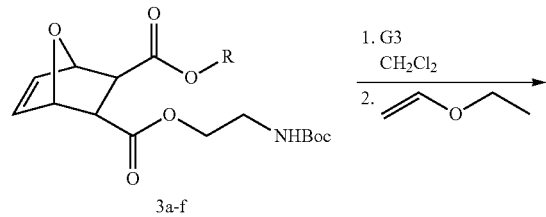

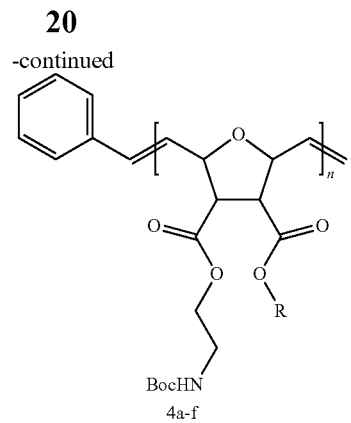

R = a Methyl
b Ethly
c Propyl
d Butyl
e Isopentyl
f Hexyl

The inventive antimicrobial polymers as defined herein may be furthermore covalently attached to a surface. In this context, the inventive antimicrobial polymers are preferably still protected, when binding same covalently to the surface, i.e. the inventive antimicrobial polymers preferably carry a protecting group, more preferably a protecting group as defined herein. Hence, even though deprotection may also be carried out in solution, the present inventive approach preferably provides a surface, which has been antimicrobially coated with the protected inventive antimicrobial polymer. Deprotection may then be carried out subsequently to coating by polymer analogous deprotection, i.e. the protecting group, e.g. the Boc protecting group, is typically completely removed after bonding to the surface with an acid such as trifluoroacetic acid (TFA) or HCl to obtain the inventive antimicrobial polymers as defined herein as covalently bound facially amphiphilic SMAMPs. Nevertheless, for the purposes of the present invention, inventive antimicrobial polymers as defined herein may usually include any polymer as defined herein, including such inventive antimicrobial polymers carrying a protection group ("precursors of the inventive antimicrobial polymers") or being deprotected, and optionally being endcapped with a terminating agent as defined herein, unless indicated otherwise.

As defined above, the inventive antimicrobial polymers as defined herein may be covalently attached to a surface. Such a surface may be any suitable surface, preferably an inorganic surface, such as e.g. surfaces containing or comprising metals or alloys, e.g. from iron, gold, silver, copper, aluminum, nickel, chrome, titanium, molybdenum, magnesium, zirconium, etc., or ceramics, titanium or zirconium oxides, etc, or an organic surface, such as oxidized poly(styrene) or poly (ethylene). Such surfaces may be furthermore a surface of a substrate, e.g. of any implant, dental implant, prosthesis, joint, bone, tooth, e.g. of an artificial joint, artificial bone, artificial tooth, inlay, etc., as well as any material used or to be used for implanting such a substrate, e.g. screws, anchors, any fastener or fixing material, etc. as well as any material used or to be used for implanting such a substrate. Such substrates may furthermore be selected from any medical or surgical device or tool, including implant trephine or trepan drill, scalpels, forceps, scissors, screws, fasteners and/or fixing material used for implantation, holders, clips, clamps, needles, linings, tubes, water tubes, pipes, water pipes, bottles and bottle inlays, inlays for medical equipment, etc., but also (surfaces of e.g.) operating tables, treatment chairs, catheter, stents, any wound dressing material, including plaster, gazes, bandages, but also bed sheets for clinical or medical purposes, sheets for covering medical devices, etc. Furthermore, surfaces or substrates may be selected from any further device, such as bindings or book covers, keyboards, computer keyboards, computer, laptops, displays, display covers, lamps, grips of tools and instruments, etc. Surfaces or substrates may also include any biomaterial suitable for tissue support, e.g. as a cell or tissue carrier system for wound dressing, or for volume preservation of solid body tissues. Surfaces or substrates may also include any substrate or surface used for storage of cells, tissue, organs, etc., but also any substrate or surface used for storage of food, such as refrigerators, coolers, storage boxes, etc.

For the purposes of the present invention, such a surface or (surface of a) substrate as defined herein may be pretreated to allow binding of further compounds, such as the inventive antimicrobial polymers or compounds needed to covalently bind these polymers. More preferably, the surface as defined above may be pretreated to allow binding of a reactive compound, e.g. a reactive silane compound or a photoreactive silane compound. Such a pretreatment may occur prior to binding the reactive compound and preferably modifies the surface to comprise, e.g., oxide or hydroxide groups, etc., and thus allow binding reactive compounds by reacting with the oxide or hydroxide groups on the surface. Accordingly, the surface may be treated prior to binding to generate e.g. hydroxide or oxide groups, e.g. with a strong base such as sodium hydroxide, ammonium hydroxide, oxygen plasma, or with UV-ozone and the like. In the case of a metal, the metal can be subject to an oxidizing potential to generate oxide or hydroxide sites on the surface of the metal. In the case of an organic material, the organic material may be likewise pretreated to comprise e.g. oxide or hydroxide groups, etc. Alternatively, the organic material already comprises e.g. oxide or hydroxide groups, etc. When binding to the surface, preferably a covalent bond forms between the surface, e.g. its oxide or hydroxide groups, and the reactive compound, e.g. a reactive silane compound or a photoreactive silane compound.

Covalently binding the inventive antimicrobial polymers to a surface as defined herein may occur via any suitable method known to a skilled person. Such methods preferably include "photocrosslinking approaches", "grafting from" and "grafting onto" techniques.

In this context, the term "photocrosslinking approach" typically means crosslinking of the inventive antimicrobial polymer to a (pretreated) surface as defined herein via a photoreactive compound. For this purpose, the (pretreated) surface is preferably further functionalized.

The term "grafting onto" typically means that the inventive antimicrobial polymer, which has preferably been functionalized with a terminating agent, e.g. terminating agent 1 or 2, preferably prepared according to a method as defined above, is covalently attached to a (pretreated) surface as defined above. Likewise, for this purpose, the (pretreated) surface is preferably further functionalized.

In contrast thereto, the term "grafting from" typically means that the inventive antimicrobial polymer is preferably polymerized starting from a monomer initiator as defined herein, which has been covalently attached to a (pretreated) surface as defined above. For this purpose, the (pretreated) surface is preferably further functionalized.

According to a first alternative, the inventive antimicrobial polymer is preferably bound to a surface or a substrate as defined herein via a photoreactive compound ("photocrosslinking approach").

According to one aspect of the photocrosslinking approach, the (pretreated) surface may be preferably further functionalized with a photoreactive silane compound. In this context, suitable photoreactive silane compounds, which may be covalently bound to such a (pretreated) surface, may comprise, without being limited thereto, e.g. any silane compound that has at least one photoreactive group thereon, e.g. silane compounds having mono-, di-, or tri-silane moieties, preferably silane compounds having at least one tri($C_1$-$C_3$)alkoxysilyl group and at least one photoreactive group as defined herein. Suitable tri($C_1$-$C_3$)alkoxysilyl groups include e.g. trimethoxysilyl, triethoxysilyl, and tripropoxysilyl, and combinations thereof. More preferably, photoreactive silane compounds may comprise, e.g., triethoxysilane benzophenone, benzoylbenzoyl)amino($C_1$-$C_3$)alkyltri($C_1$-$C_3$)alkoxy silane, (4-benzoylbenzoyl)aminopropyltrimethoxy silane, (4-benzoylbenzoyl)aminoethyltrimethoxy silane, and 4-(3'-chlorodimethylsilyl)propyloxybenzophenone. Such photoreactive silane compounds can be desirable because they can both bind the (pretreated) surface and then, after photoactivation, bind the inventive antimicrobial polymer. Therefore, the binding procedure of a further compound to the surface, such as the inventive antimicrobial polymer, can be simplified because only one compound needs to be applied. Binding of the photoreactive silane compound to the (pretreated) surface preferably occurs via the silane moiety, and further binding of the inventive antimicrobial polymer preferably occurs via the at least one photoreactive moiety of the photoreactive silane compound.

According to a further aspect of the photocrosslinking approach, the (pretreated) surface may be preferably further functionalized with a reactive silane compound, which does not comprise a photoreactive moiety. In this context, the reactive silane compound is preferably covalently bound to the (pretreated) surface as defined herein in a first step. Then, preferably, a photoreactive crosslinking agent is bound to the silane, e.g. via a reactive moiety of the silane, e.g. a —COOH moiety. In a final step, preferably the inventive antimicrobial polymer is covalently bound via the photoreactive moiety of the photoreactive crosslinking agent in a photocrosslinking reaction, e.g. via UV activation.

In this context, a reactive silane compound, which does not comprise a photoreactive moiety and which may be covalently bound to the (pretreated) surface as defined herein in a first step, is preferably selected from silane compounds having at least one or at least two tri($C_1$-$C_3$)alkoxysilyl groups. Such silane compounds may provide a more hydrolytically stable bond to the substrate at least because each tri($C_1$-$C_3$)alkoxysilyl group can result in a bond (Si—O-Metal) with the surface. Examples of suitable tri($C_1$-$C_3$) alkoxysilyl containing silane compounds include, but are not limited to, bis(trimethoxysilyl)hexane, bis(trimethyoxysilyl) ethane, and bis(trimethoxysilylethyl)benzene, preferably 1,4-bis(trimethoxysilylethyl)benzene. Furthermore, a mixture of these reactive silane compounds, preferably of tri($C_1$-$C_3$)alkoxysilyl silane compounds, can be used. The silane compound may also include [gamma]-methacryloxypropyltrimethoxysilane, either alone or in combination with other silanes, e.g. [gamma]-methacryloxypropyltrimethoxysilane and 1,4-bis(trimethoxysilylethyl)benzene. The silane compound may also have hydrophobic properties, e.g. selected from 3-(3-methoxy-4-methacryloyloxyphenyl) propyltrimethoxysilane. Additionally, the reactive silane compound may be selected from e.g. dimethyl chlorosilane, methyldichlorosilane or trichlorosilane. In the latter cases (also for all chlorosilanes), the silanization reaction is preferably carried out under exclusion of moisture in dry toluene and in the presence of a base, e.g. triethylamine.

Furthermore, a photoreactive crosslinking agent, which may be bound to the (preferably already covalently bound) reactive silane compound in a second step, may be selected from any suitable photoreactive crosslinking agent known to a skilled person to be photoreactive. Furthermore, such a photoreactive crosslinking agent has preferably at least one latent photoreactive group that can become chemically reactive when exposed to an appropriate energy source, e.g. UV-radiation (UV-activation), visible light, microwaves, etc. As used herein, the phrase "photoreactive group" refers to a chemical moiety that is sufficiently stable to remain in an inactive state (i.e., ground state) under normal storage conditions but that can undergo a transformation from the inactive state to an activated state when subjected to an appropriate energy source. Photoreactive groups respond to specific applied external stimuli to undergo active species generation with resultant covalent bonding to an adjacent chemical structure, e.g., as provided by the same or a different molecule. Photoreactive groups can thus be chosen to be responsive to an appropriate energy source, e.g. UV-radiation, visible light/radiation, microwaves, etc. Suitable photoreactive groups in the context of the present invention include, for example, azides, diazos, diazirines, ketones, and quinones. Upon "activation" with an appropriate energy source, the photoreactive group generates an active species such as free radicals including, for example, nitrenes, carbenes, and excited states of ketones.

According to one specific aspect of the photocrosslinking approach, each photoreactive group on the photoreactive crosslinking agent can abstract e.g. a hydrogen atom from an alkyl group on either the silane compounds, the hydrolysis reaction product of the silane compound, the polymeric reaction product formed from the hydrolysis reaction product of the silane compound, or a combination thereof, and/or the inventive antimicrobial polymer as defined above to be covalently bound. By covalently binding to both the silane compound and the inventive antimicrobial polymer, the photoreactive crosslinking agent promotes adhesion and/or increases binding strength.

Preferably, the photoreactive crosslinking agent is an aryl ketone, such as acetophenone, benzophenone, anthrone, and anthrone-like heterocycles (i.e., heterocyclic analogs of anthrone such as those having N, O, or S in the 10-position), or their substituted (e.g., ring substituted) derivatives. Examples of aryl ketones include heterocyclic derivatives of anthrone, including acridone, xanthone, and thioxanthone, and their ring substituted derivatives. Other suitable photoreactive crosslinking agent include quinone such as, for example anthraquinone. The functional groups of such aryl ketones can undergo multiple activation/inactivation/reactivation cycles. For example, benzophenone is capable of photochemical excitation with the initial formation of an excited singlet state that undergoes intersystem crossing to the triplet state. The excited triplet state can insert into carbon-hydrogen bonds by abstraction of a hydrogen atom (from a polymeric coating layer, for example), thus creating a radical pair. Subsequent collapse of the radical pair leads to formation of a new carbon-carbon bond. The radical pair, or free radical, can also be used to incite chain polymerization if the appropriate monomer species are present. If a reactive bond (e.g., carbon/hydrogen) is not available for bonding, the ultraviolet light-induced excitation of the benzophenone group is reversible and the molecule returns to ground state energy level upon removal of the energy source.

Alternatively, the photoreactive crosslinking agent may be selected from e.g. arylazides ($C_6R_5N_3$) such as phenyl azide and 4-fluoro-3-nitrophenyl azide; acyl azides (—CO—$N_3$) such as benzoyl azide and p-methylbenzoyl azide; azido formates (—O—CO—$N_3$) such as ethyl azidoformate and phenyl azidoformate; sulfonyl azides (—$SO_2$—$N_3$) such as benzenesulfonyl azide; and phosphoryl azides $(RO)_2PON_3$ such as diphenyl phosphoryl azide and diethyl phosphoryl azide, or diazo compounds constitute another class of photoreactive groups and include diazoalkanes (—$CHN_2$) such as diazomethane and diphenyldiazomethane; diazoketones (—CO—$CHN_2$) such as diazoacetophenone and 1-trifluoromethyl-1-diazo-2-pentanone; diazoacetates (—O—CO—$CHN_2$) such as t-butyl diazoacetate and phenyl diazoacetate; and beta-keto-alpha-diazoacetates (—CO—$CN_2$—CO—O—) such as t-butyl alpha diazoacetoacetate; etc. R may be preferably hydrogen or an alkyl as defined above.

Other photoreactive groups include the diazirines (—$CHN_2$) such as 3-trifluoromethyl-3-phenyldiazirine; and ketenes CH—C—O) such as ketene and diphenylketene.

Preferably, photocrosslinking of the inventive antimicrobial polymer to the photoreactive group of the photoreactive crosslinking agent, which has been covalently bound to a reactive silane as defined herein, which is further covalently bound to a (pretreated) surface as defined herein, or photocrosslinking of the inventive antimicrobial polymer to the photoreactive group of the photoreactive silane compound, which has been covalently bound to a (pretreated) surface as defined herein, usually occurs via photoactivation involving one or more photoreactive moieties of the photoreactive crosslinking agent or the photoreactive silane compound. Such a photoactivation typically involves addition of an appropriate energy source as defined above, e.g. UV-radiation, visible light, microwaves, etc., preferably sufficient to allow covalent binding of the photoreactive moiety to the inventive antimicrobial polymer. Preferably, the inventive antimicrobial polymer is bound via UV-radiation (UV-mediated crosslinking). More preferably, the integral light intensity at the sample location is typically about 50 to 150 mW $cm^{-2}$, preferably about 75 to 125 mW $cm^{-2}$, more preferably about 90 to 110 mW $cm^{-2}$, e.g. about 100 mW $cm^{-2}$. For UV-activation any suitable energy source may be applied known to a skilled person, e.g. a high-pressure mercury UV lamp, such as a high-pressure mercury UV lamp (e.g. 500 W, preferably from Oriel), or a StrataLinker 2400 (75 W, Stratagene). UV-activation may be about 2-300 min.

According to one particular preferred aspect of the "photocrosslinking approach", a surface as defined herein is preferably coated with an antimicrobial polymer as defined herein according to the following steps:
a) pretreating a surface of a substrate as defined herein to comprise oxide or hydroxide groups;
b) functionalizing the pretreated surface by covalently binding a reactive silane compound as defined herein to the pretreated surface as obtained according to step a);
c) further covalently binding of a photoreactive crosslinking agent as defined herein to the covalently bound silane compound obtained according to step b);
d) coating the surface with the (protected) inventive antimicrobial polymer as prepared according to the present invention onto the surface as obtained according to step c),
e) irradiating the photoreactive crosslinking agent with UV light thereby covalently binding the (protected) inventive antimicrobial polymer to a photoreactive group of the photoreactive crosslinking agent, thereby covalently binding the inventive antimicrobial polymer to the surface.

f) optionally carrying out a post-irradiation treatment of the covalently bound inventive antimicrobial polymer as obtained by step e) by deprotection as defined herein, e.g. with an acid as defined herein, and/or carrying out washing steps.

The steps may be carried out as generally defined herein.

According to one even further preferred aspect of the "photocrosslinking approach", a surface as defined herein is preferably coated with a (protected) antimicrobial polymer as defined herein according to the following Scheme-5:

Scheme-5: shows functionalization steps as used for attaching the inventive antimicrobial polymers as described herein onto a surface according to the "photocrosslinking approach". The shown photoreactive silane reactive compound is merely illustrative but not intended to be limiting.

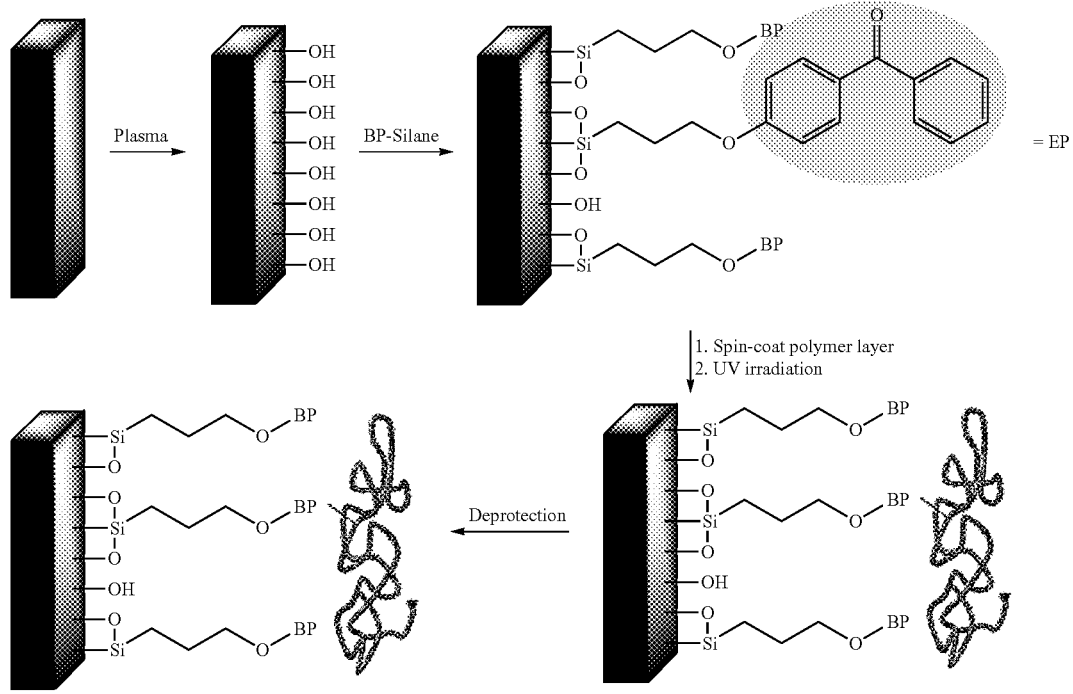

According to another particular preferred aspect of the "photocrosslinking approach", a surface as defined herein is preferably coated with an antimicrobial polymer as defined herein according to the following steps:
a) pretreating a surface of a substrate as defined herein to comprise oxide or hydroxide groups;
b) functionalizing the pretreated surface by covalently binding a photoreactive silane compound as defined herein to the pretreated surface as obtained according to step a);
c) coating the surface with the (protected) inventive antimicrobial polymer as prepared according to the present invention onto the surface as obtained according to step b),
d) irradiating the photoreactive crosslinking agent with UV light thereby covalently binding the (protected) inventive antimicrobial polymer to a photoreactive group of the photoreactive silane compound, thereby covalently binding the inventive antimicrobial polymer to the surface.
e) optionally carrying out a post-irradiation treatment of the covalently bound inventive antimicrobial polymer as obtained by step d) by deprotection as defined herein, e.g. with an acid as defined herein, and/or carrying out washing steps.

The steps may be carried out as generally defined herein.

According to a second alternative, the inventive antimicrobial polymer is preferably bound to a surface or a substrate as defined herein via "grafting onto". For this purpose, the (pretreated) surface is preferably functionalized with a reactive silane compound as defined above, having no photoreactive moiety, e.g. a chlorodimethyl silane bearing a primary amine, or a dichloromethyl silane, or a trichloromethylsilane, preferably also bearing a primary amine, etc. Furthermore, the inventive antimicrobial polymer as defined herein has been preferably end-functionalized with a terminating agent, preferably with a terminating agent as defined herein, more preferably terminating agent 1 or 2. For this purpose, the polymerization of the living polymer as defined above may be terminated by e.g. termination agents 1 or 2 as defined above. More preferably, the polymerization of the living polymer as defined above may be terminated by termination agent 2 as defined above. This reaction product, i.e. an end-functionalized (protected) antimicrobial polymer as defined according to the present invention, may then be reacted with a (pretreated) surface preferably functionalized with a reactive silane compound as defined above, more preferably using DMF and DMAP. This reaction does not require any photoactivation.

According to one particular preferred aspect of "grafting onto", a surface as defined herein is preferably coated with an antimicrobial polymer as defined herein according to the following steps:
a) pretreating a surface of a substrate as defined herein to comprise oxide or hydroxide groups;
b) functionalizing the pretreated surface by covalently binding a reactive silane compound as defined herein to the pretreated surface as obtained according to step a);
c) binding the inventive end-functionalized (protected) antimicrobial polymer as prepared according to the present invention to the reactive silane compound of the functionalized surface as obtained according to step b), thereby covalently binding the inventive end-functionalized (protected) antimicrobial polymer to the surface;

d) optionally carrying out a post-"grafting onto" treatment of the covalently bound inventive antimicrobial polymer as obtained by step c) by deprotection as defined herein, e.g. with an acid as defined herein, and/or carrying out washing steps.

The steps may be carried out as generally defined herein.

According to one even further preferred aspect of "grafting onto", a surface as defined herein is preferably coated with an antimicrobial polymer as defined herein according to the following Scheme-6:

Scheme-6: shows functionalization steps as used for grafting the inventive antimicrobial polymers as described herein onto a surface according to the present invention. The shown reactive silane reactive compound and the funtional residues of the inventive antimicrobial polymer are merely illustrative but not intended to be limiting.

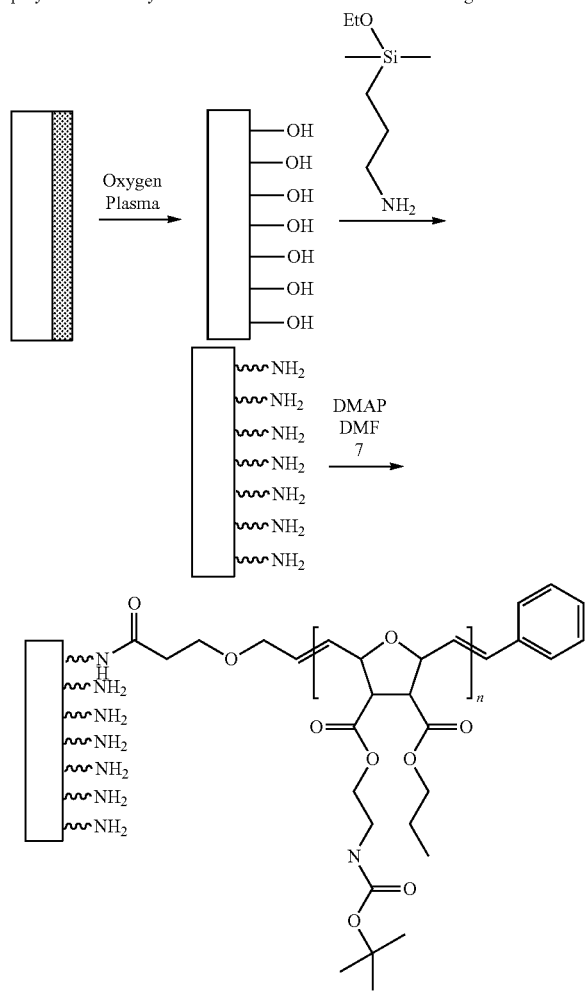

According to a third alternative, the inventive antimicrobial polymer is preferably bound to a surface or a substrate as defined herein via "grafting from". For this purpose, a (pretreated) surface as defined herein is preferably functionalized with an alkenyl- or norbornenyl-containing silane. Such an alkenyl- or norbornenyl-containing silane may be selected, e.g., from a reactive silane compound as defined above, which does not comprise a photoreactive moiety, which may be covalently bound to the (pretreated) surface as defined herein in a first step, and which additionally contains an alkenyl- or norbornenyl-moiety. Such an alkenyl-containing silane compound is preferably selected from alkenyl- or norbornenyl-containing silane compound having at least one or at least two tri($C_1$-$C_3$)alkoxysilyl groups. Such alkenyl- or norbornenyl-containing silane compound may provide a more hydrolytically stable bond to the substrate at least because each tri($C_1$-$C_3$)alkoxysilyl group can result in a bond (Si—O-Metal) with the surface. Examples may include e.g. 7-octenyl trimethoxysilane, norbornenyl-silane, oxanorbornenyl-silane, etc. The silanization reaction is preferably carried out under exclusion of moisture in dry toluene and in the presence of a base, e.g. triethylamine. These alkenyl- or norbornenyl-containing silanes may also be mixed with a nonreactive silane, e.g. n-propyltrimethoxysilane, and used to functionalize the (pretreated) surface to dilute (and reduce) the number of initiating sites on the surface. Having bound the alkenyl-containing silane to the (pretreated) surface, this functionalized surface, preferably, the alkenyl- or norbornenyl-containing silane, is then exposed to the metathesis reaction initiator (Grubbs $2^{nd}$ generation catalyst, benzylidene[1,3-bis(2,4,6-trimethylphenyl)-2-imidazolidinylidene]dichloro(tricyclohexylphosphine)ruthenium). Polymerization is then preferably started from the thus created covalently bound ruthenium species upon addition of a monomer according to any of formulae (I), (I') and (I") The reaction conditions for the polymerization reaction are preferably as defined above for the polymerization of monomers as defined according to any of formulae (I), (I') and (I").

According to one particular preferred aspect of "grafting from", a surface as defined herein is preferably coated with an antimicrobial polymer as defined herein according to the following steps:

a) pretreating a surface of a substrate as defined herein to comprise oxide or hydroxide groups;

b) functionalizing the pretreated surface by covalently binding a reactive alkenyl- or norbornenyl-containing silane compound as defined herein to the pretreated surface as obtained according to step a);

c) reacting Grubbs $2^{nd}$ generation catalyst with the covalently bound norbornenyl- or alkenyl-containing moiety of the silane, thereby leading to a surface-bound ruthenium species;

d) adding a monomer according to any of formulae (I), (I') and (I") as defined herein and initiating an in-situ polymerization of the monomer by the surface-bound ruthenium species obtained according to step c), thereby providing an in-situ polymerized (protected) inventive antimicrobial polymer covalently bound to the surface, e) terminating the polymerization reaction of step d) by adding a terminating agent as defined herein, preferably ethylvinylether, terminating agent 1, or terminating agent 2;

f) optional carrying out a post-"grafting from" treatment of the covalently bound (protected) inventive antimicrobial polymer as obtained by step e) by deprotection as defined herein, e.g. with an acid as defined herein, and/or carrying out washing steps.

The steps may be carried out as generally defined herein.

Preferably, the catalyst is solved in non-polar solvent as defined herein, preferably dichloromethane, e.g. about 5 mM. Likewise preferably, the components are applied to the surface under a controlled atmosphere, preferably $N_2$ or argon. The compounds are preferably incubated for about 10 minutes, and washed. Preferably, the monomers as defined according to any of formulae (I), (I') and (I") as defined herein, are solubilized in a non-polar solvent as defined herein, preferably dichloromethane, toluene, tetrachloroethane, etc., or a (further) ionic liquid. Likewise preferably, the components are applied to the surface under a controlled atmosphere, preferably $N_2$ or argon. The monomer concentration of the monomers as defined according to any of formulae (I), (I') and (I") as defined herein is preferably about 0.005 to about 0.01 mM, more preferably about 0.01 to about 0.1 mM, e.g. about 0.05 mM. The compounds are preferably incubated for about 10 minutes, and preferably quenched with a terminating agent as defined herein, e.g. ethylvinylether.

According to one even further preferred aspect of "grafting from", a surface as defined herein is preferably coated with an antimicrobial polymer as defined herein according to the following Scheme-7:

Scheme-7: shows functionalization steps as used for grafting the inventive antimicrobial polymers as described herein from a surface according to the present invention by in-situ polymerization. The shown reactive silane reactive compounds are merely illustrative but not intended to be limiting.

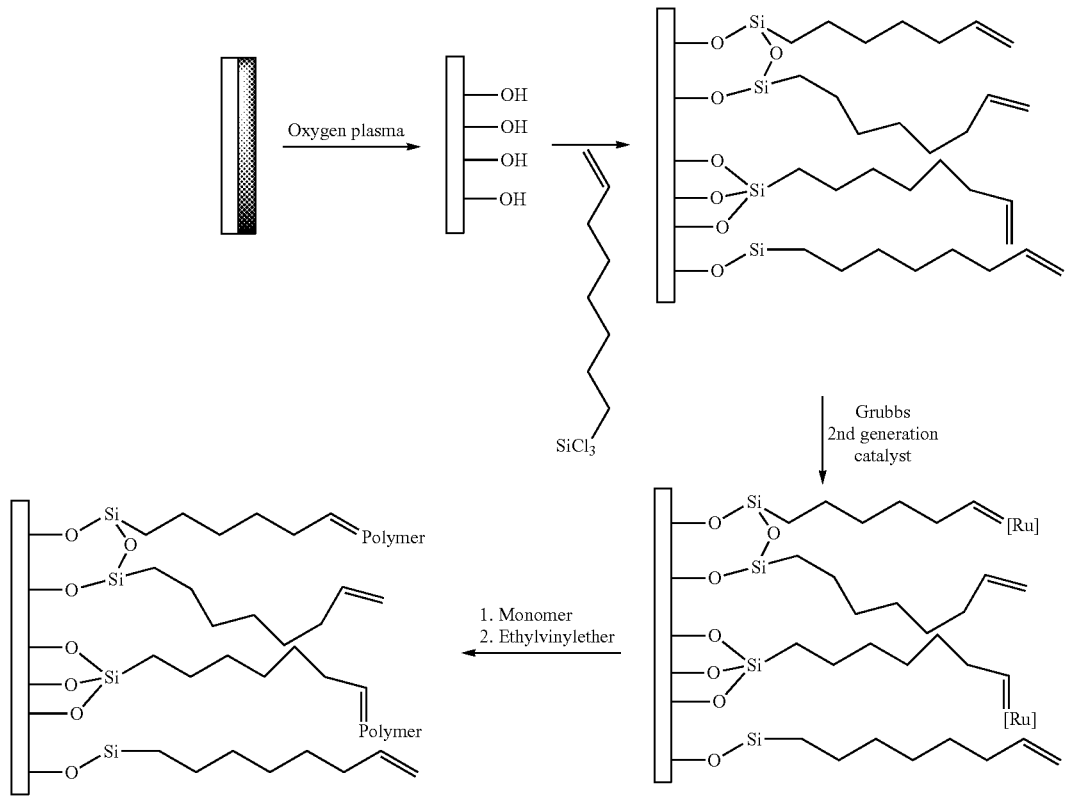

The inventive (protected or deprotected) antimicrobial polymers as defined herein may exhibit a molecular weight from about 1,000 to about 1,000,000 g mol$^{-1}$, preferably a molecular weight from about 3,000 to about 1,000,000 g mol$^{-1}$, more preferably a molecular weight of more than 100,000 g mol$^{-1}$, preferably when covalently bound to a surface or a substrate as defined herein using grafting from as defined herein.

Applying the different compounds as defined above to the surface as defined herein, e.g. the photoreactive silane compound, the reactive silane compound, the photoreactive crosslinking agent and/or the inventive antimicrobial monomers or polymers as defined herein to a surface as defined herein, may occur using any technique suitable for a skilled person to apply a liquid or semi-liquid compound to a surface, e.g. via a technique, such as immersion, spraying, spin coating or dip coating, pouring, etc., preferably via spin-coating or dip-coating.

In this context, "spin coating" is typically a procedure used to apply uniform thin films to flat or other surfaces of a substrate, wherein an excess amount of a solution is usually placed on the surface, which is then rotated at high speed in order to spread the excess fluid by centrifugal force. Machines suitable for the inventive purpose preferably include spin coater or spinner. Typically, four distinct stages may be defined during the spin coating process: 1) Deposition of the coating fluid onto the surface of a substrate, e.g. by using a nozzle, pouring the coating solution or by spraying it onto the surface. A substantial excess of coating solution is usually applied compared to the amount that is required. 2) Acceleration of the substrate up to a final, desired, rotation speed. 3) Spinning of the substrate at a constant rate, wherein fluid viscous forces dominate the fluid thinning behavior. 4) Optionally spinning of the substrate at a constant rate, wherein solvent evaporation dominates the coating thinning behavior. In the continuous process, the steps are carried out directly after each other.

Furthermore, "dip-coating" is typically a procedure used to apply uniform thin films onto flat or cylindrical/round-shaped surfaces of substrates and typically can be separated into five stages: 1) Immersion: The substrate is preferably immersed in the solution of the coating material, either without or at a constant speed. 2) Start-up: The substrate preferably remains inside the solution for a while and is started to been pulled up.

3) Deposition: The thin layer is preferably deposited on the substrate while it is pulled up. The withdrawing is carried out by rotating at a preferably constant speed. The speed determines the thickness of the coating. 4) Drainage: Excess liquid usually drains from the surface. 5) Optionally evaporation: The solvent may evaporate from the liquid, forming the thin layer. In the continuous process, the steps are carried out directly after each other.

Preferably, the surface as defined above, preferably a pretreated and with a reactive silane (and a photoreactive crosslinker agent) functionalized surface or a pretreated and with a photoreactive silane functionalized surface, may be coated with a further compound as defined above, e.g. the (protected) inventive antimicrobial polymer as defined herein or any further compound via spin coating or dip-coating, preferably via spin-coating.

As defined above, the inventive antimicrobial polymers as defined herein may be covalently bound to a surface, to obtain an antimicrobially coated surface. Such a surface coating layer may comprise a thickness of about 2 nm to about 1 µm. The thickness of the antimicrobial surface coating layer may be dependent on the different methods used for application. Preferably, the thickness of the antimicrobial surface coating layer, comprising the protected or already deprotected inventive antimicrobial polymer, may be about 50 nm to about 500 nm, when using the photocrosslinking approach as defined herein, more preferably about 4 to 40 µm after washing and/or deprotection. Alternatively, the thickness of the antimicrobial surface coating layer, comprising the protected or already deprotected inventive antimicrobial polymer, may be about 5 nm to about 20 nm, when using the grafting onto approach as defined herein, wherein the thickness of the antimicrobial surface coating layer is typically dependent on the length of the polymer to be covalently bound. Finally, the thickness of the antimicrobial surface coating layer may be about 5 nm to about 1 µm when using the grafting from approach as defined herein, wherein the thickness of the antimicrobial surface coating layer is typically dependent on the reaction time and thus from the obtained length of the polymer covalently bound.

As defined above, the inventive antimicrobial polymers as defined herein may be covalently bound to a surface or substrate as defined above, to obtain an antimicrobially coated surface. Accordingly, as a further embodiment, the present invention also provides a surface or a substrate as defined above comprising an inventive (protected or deprotected) antimicrobial polymer covalently bound to the surface (of the substrate).

According to a further preferred embodiment, the present invention also provides the use of an inventive antimicrobial polymer as defined herein for antimicrobially coating a surface or substrate as defined herein by covalently binding the (protected or deprotected) inventive antimicrobial polymer to the surface or substrate as defined herein, preferably via photoactivation.

According to final preferred embodiment, the present invention also provides the use of an inventive (protected or deprotected) antimicrobial polymer as defined herein, preferably covalently bound to a surface as defined herein, preferably to a surface of a substrate as defined herein, for inhibiting the growth of bacteria, thereby preferably exhibiting a low toxicity to human cells. In this context, the covalently bound inventive (protected or deprotected) antimicrobial polymers preferably show significant growth reduction of bacterial pathogens on a surface of at least about 7%, preferably at least about 70%, more preferably at least about 80%, even more preferably at least about 90%, likewise even more preferably at least about 95, 96, 97, 98, 99 or 99.99%, preferably of *S. aureus* and *E. faecalis*. As an example, the covalently bound inventive antimicrobial polymer with R=propyl preferably reduces growth of *S. aureus* about 99.99% and *E. faecalis* about 97%. The covalently bound inventive antimicrobial polymers are preferably also benign to mammalian cells, e.g. the polymer with R=propyl does not impair proliferation of gingiva fibroblasts.

FIGURES

The figures shown in the following are merely illustrative and shall describe the present invention in a further way. These figures shall not be construed to limit the present invention thereto.

FIG. 1: shows results of an atomic force microscopy measurement on silicon wafer as described herein, which have been covalently coated with inventive antimicrobial polymers with R=propyl. The thickness of the layer of the inventive antimicrobial polymers was found to be 20 nm as determined via ellipsometric analysis. Atomic force microscopy revealed a coarseness or roughness of about 8.4 nm. A line scan along the line shown in the micrograph is also shown.

Figure 2:
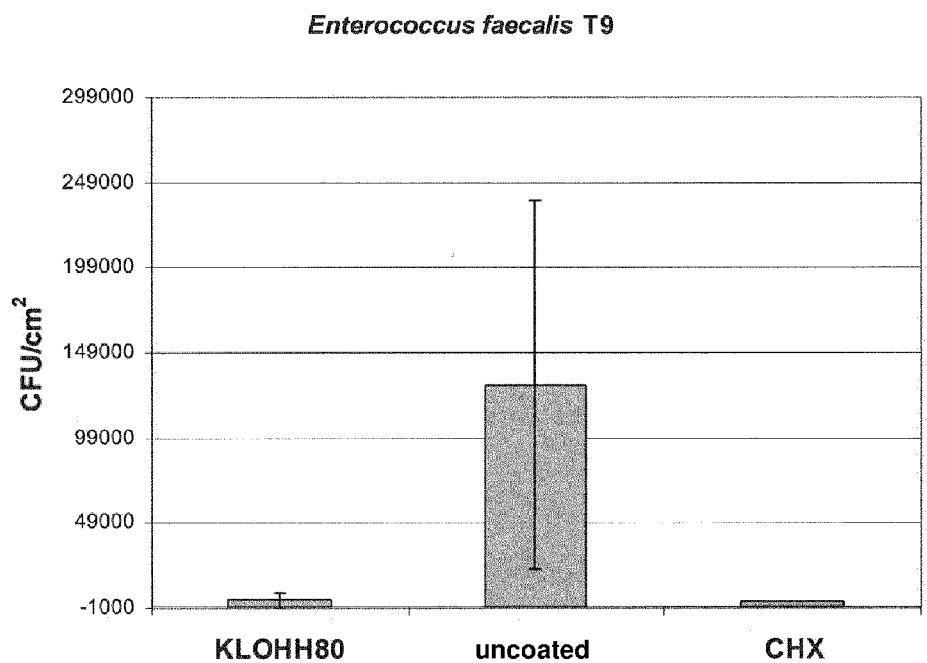

FIG. 2: shows the results of the determination of the antimicrobial activity of inventive antimicrobial polymers with R=propyl when covalently bound to a silicon wafer. As can be seen, covalently binding the inventive antimicrobial polymers to the modified silicon wafer led to a significant reduction of pathogens cultured from *Enterococcus faecalis* of at least two steps in the logarithmic scale (the inventive antimicrobial polymers are indicated as KL0HH80 (R=propyl).

Figure 3:
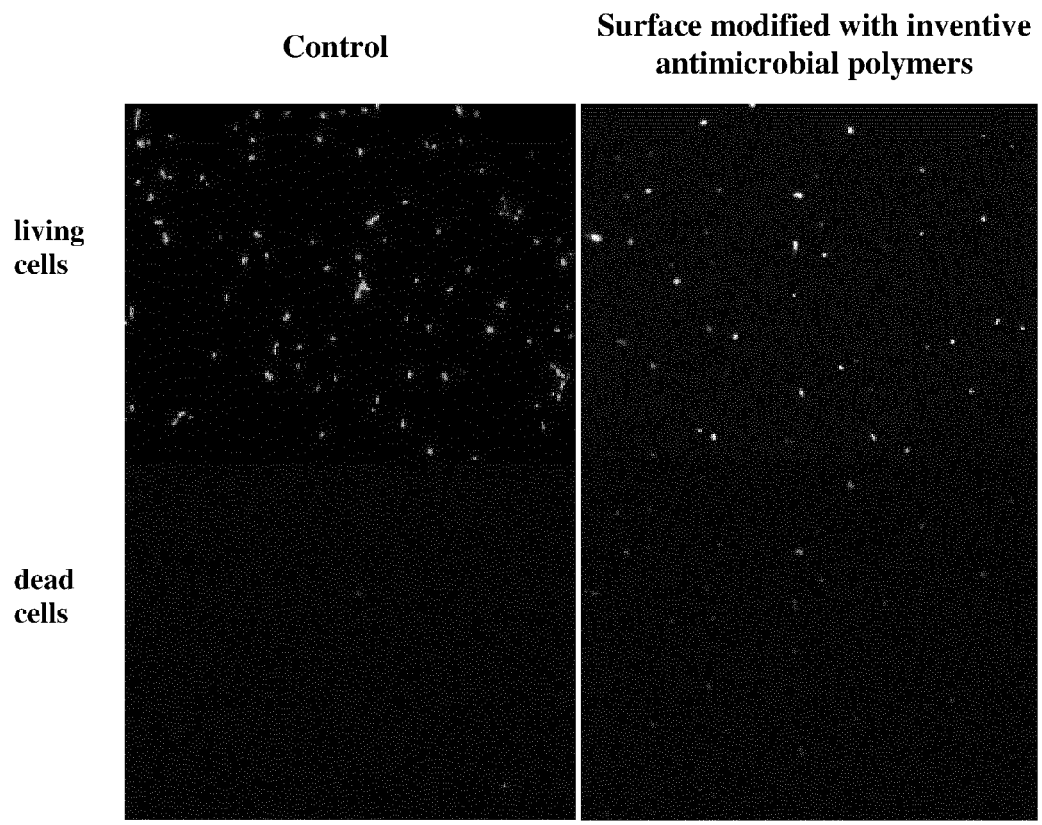

FIG. 3: shows live/dead staining of silicon wafers, to which inventive antimicrobial polymers (R=propyl) have been bound covalently. Uncoated silicon wafers are shown as a control). The treated modified silicon wafer and the untreated silicon wafer (control) were subjected to a live/dead staining. As can be seen, the treated modified silicon wafer shows a higher number of membrane compromised cells (=red dead cells) from *Enterococcus faecalis* stained with propidium iodide (living cells) (right column, upper row), when compared to vital cells stained with SYTO9 (right column, lower row).

EXAMPLES

The examples shown in the following are merely illustrative and shall describe the present invention in a further way. These examples shall not be construed to limit the present invention thereto.

1—General:

All chemicals were obtained as reagent grade from Aldrich, Fluka or Acros and used as received. HPLC grade solvents were purchased from Aldrich or Acros and used as received. THF (HPLC grade, Fisher Scientific) was distilled from sodium/benzophenone under nitrogen. Dichloromethane (HPLC grade, Fisher Scientific) was distilled from $CaH_2$ under nitrogen.

Gel permeation chromatography (DMF/0.01 M LiCl, calibrated with polystyrene standards) was measured on a PSS GRAM column (PSS, Mainz, Germany). NMR spectra were recorded on a Bruker 250 MHz spectrometer (Bruker, Madison, Wis., USA).

2—Synthesis of a Variation of Grubbs $3^{rd}$ Generation Catalyst

A variation of Grubbs $3^{rd}$ generation catalyst (original Grubbs $3^{rd}$ generation catalyst=Dichloro-di(3-bromopyridino)-N,N'-Dimesitylenoimidazolino-Ru=CHPh; G3) was specifically synthesized similar as described previously by Grubbs and colleagues (see J. A. Love, J. P. Morgan, T. M. Trnka, R. H. Grubbs, Angewandte Chemie International Edition 2002, 41, 4035-4037). For this variation of Grubbs $3^{rd}$ generation catalyst pyridine was taken instead of 2-bromo pyridine to yield the corresponding catalyst with two pyridine ligands.

3—Terminating Agents a) Ethylvinylether

Ethylvinylether was obtained as reagent grade from Aldrich, Fluka or Acros.

b) Synthesis of Terminating Agent 1

Compound A was synthesized as described in the literature (see above). Compound A (2.0 g, 6.95 mmol), pentafluorphenol (3.2 g, 17.4 mmol) and DMAP (0.21 g, 1.74 mmol) were dissolved in 50 mL dry DCM under $N_2$. The resulting solution was then cooled to 0° C., and EDC (3.33 g, 17.4 mmol) was added to the mixture in portions. The reaction mixture was then allowed to warm to room temperature and stirred for another 12 hours. The mixture was then washed with 10% $KHSO_4$ solution, saturated $NaHCO_3$ solution, and brine. The resulting DCM solution was dried using anhydrous $Na_2SO_4$, filtered, and the solvent was evaporated. The resulting residue was purified by filtration through a neutral alumina plug using DCM as eluent, to afford 2.59 g of white solid (yield=60%).

$^1$H-NMR (300 MHz, $CDCl_3$): 5.77 (m, 2H, =CH), 4.75 (d, J=5.6 Hz, 4H, =CH—$CH_2$), 3.05 (t, J=6.2 Hz, 4H, OOC—$CH_2$—$CH_2$), 2.95 (t, J=6.2 Hz, 4H, OOC—$CH_2$—$CH_2$—COO—$C_6F_5$). $^{13}$C-NMR (75 MHz, $CDCl_3$): 171.1 (C=O—O allylic); 168.4 (C=O—O—$C_6F_5$); 142.9, 141.7, 139.5, 137.8 & 136.1 (m, $F_5C_6$); 127.9 (C=C), 60.5 ($CH_2$—C=C), 28.7 & 28.3 ($CH_2$—$CH_2$). MS-FAB: 620.0 (M), 621.0 (M+1), 622 (M+2).

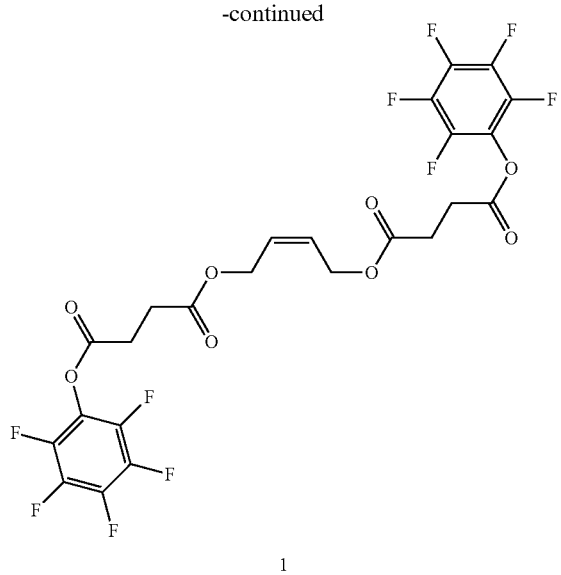

1 c) Synthesis of Terminating Agent 2

10.0 g cis-2-butene-1,4-diol (114 mmol, 1.0 eq) and 36.4 g (284 mmol, 2.5 eq) tert-butyl acrylate were mixed with 200 mL THF. Catalytic amounts of water and sodium hydroxide were added. The reaction was stirred at room temperature for three days, after which the solvent was evaporated. The product (monoadduct of the Michael addition) and tert-butyl acrylate were dissolved in 100 mL DMSO, adding catalytic amounts of water and sodium hydroxide. After two days, 500 mL of water were added. The mixture was extracted three times with dichloromethane. The organic layers were combined, washed with 10% $KHSO_4$ (3×) and 10% $NaHCO_3$ (3×), and dried over $MgSO_4$. After filtering, the solvent and excess acrylate were removed by evaporation (rotary evaporator, followed by high vacuum). The crude product B (yield 95%) was taken to the next reaction step.

$^1$H-NMR (300 MHz, $CDCl_3$): 5.79 (m, 2H, =CH), 4.04 (d, J=4.7 Hz, 4H, =CH—$CH_2$), 3.64 (t, J=6.4 Hz, 4H, O—$CH_2$—$CH_2$), 2.48 (t, J=6.4 Hz, 4H, O—$CH_2$—$CH_2$), 1.44 (s, 18H, t-butyl).

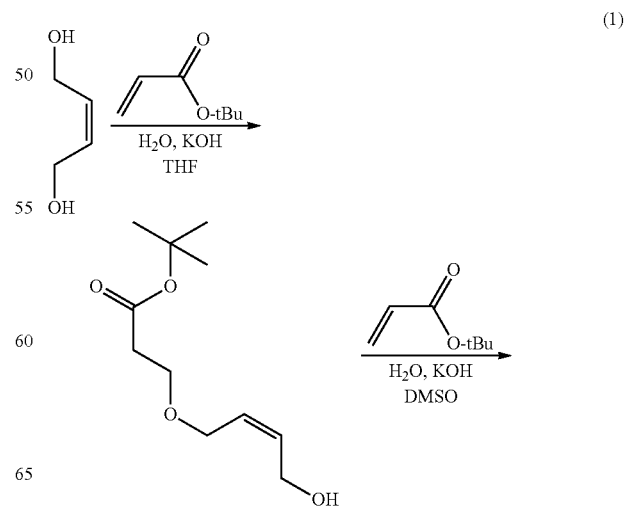

(1)

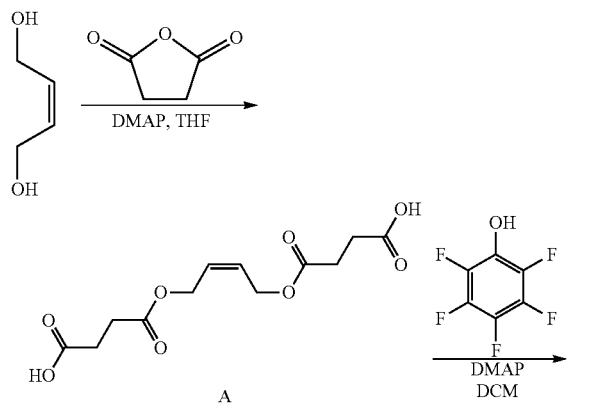

A

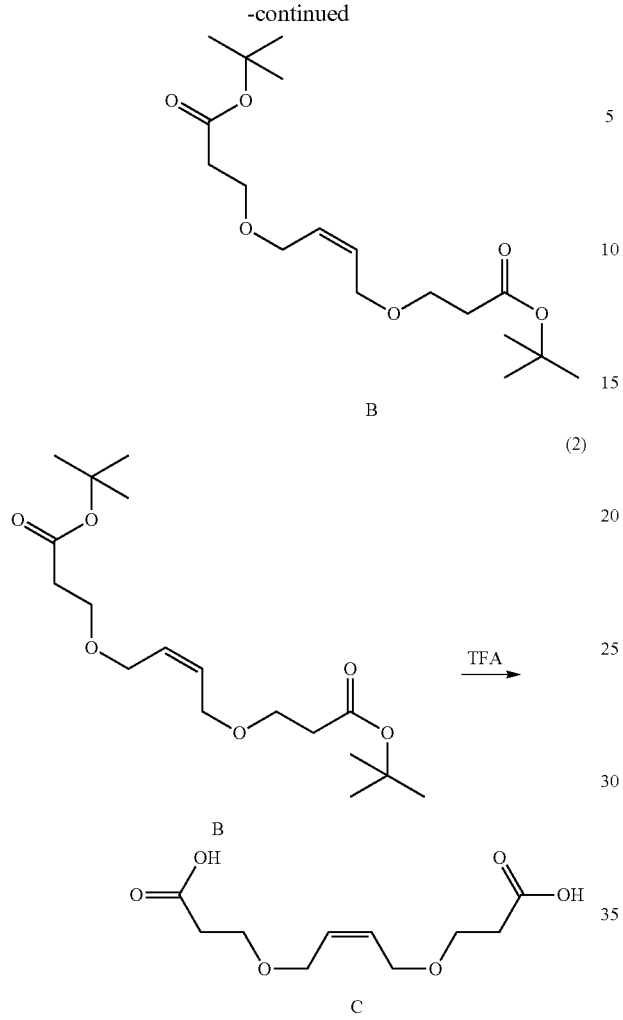

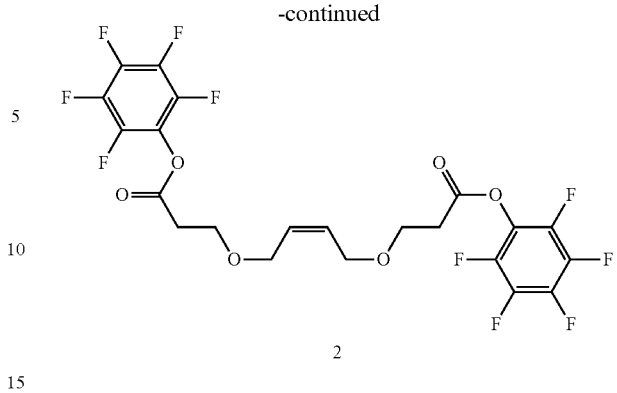

2.69 g (11.6 mmol, 1 eq) C were dissolved in 50 mL anhydrous dichloromethane under nitrogen. Catalytic amounts of 4-dimethylaminopyridine and 6.40 g (34.8 mmol, 3 eq) pentafluorophenol were added. The reaction mixture was cooled to 0° C., and 6.68 g (34.8 mmol, 3 eq) of 1-ethyl-3-(3-dimethylaminopropyl)carbodiimid was added. The reaction was stirred over night. It was then washed with 10% KHSO$_4$ (2×), water (1×) and 10% NaHCO$_3$ (2×), and dried over MgSO$_4$. After filtering, the solvent was evaporated and the product was vacuum dried.

$^1$H-NMR (300 MHz, CDCl$_3$): 5.77 (m, 2H, =CH), 4.14 (d, J=5.4 Hz, 4H, =CH—CH$_2$), 3.84 (t, J=6.2 Hz, 4H, O—CH$_2$—CH$_2$), 2.95 (t, J=6.2 Hz, 4H, O—CH$_2$—CH$_2$). $^{13}$C-NMR (75 MHz, CDCl$_3$): 167.5 (C=O—O); 143.2, 141.2, 139.8, 139.8 & 136.3 (m, F$_5$C$_6$); 128.2 (C=C), 67.0 (O—CH$_2$—C=C), 64.5 (CH$_2$—CH$_2$—O); 34.5 (CH$_2$—COO—C$_6$F$_5$). MS-FAB: 562 (M−2), 563 (M−1), 564 (M), 565 (M+1), 566 (M+2).

4—Preparation of Monomers:

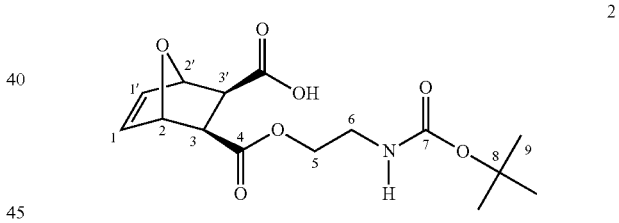

The monomer 2 was obtained from exo-7-oxabicyclo[2.2.1]hept-5-ene-2,3-dicarboxylic acid anhydride 1 (5 g, 30.0 mmol),

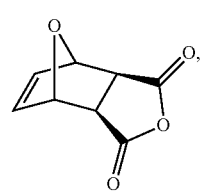

5.00 g (14.5 mmol) of B were dissolved in a mixture of 15 mL trifluoroacetic acid and 15 mL dichloromethane. After stirring over night at room temperature, the solvent was removed at the rotovap. 50 mL dichloromethane was added and evaporated three times (azeotropic removal of excess acid). The crude product C, obtained with quantitative conversion according to NMR, was dried in high vacuum. The solid was recrystallized from hexane/ethylacetate.

$^1$H-NMR (300 MHz, CDCl$_3$): 8.04 (br s, 2H, COOH), 5.73 (m, 2H, =CH), 4.08 (d, J=6.1 Hz, 4H, =CH—CH$_2$), 3.71 (t, J=6.1 Hz, 4H, O—CH$_2$—CH$_2$), 2.63 (t, J=6.1 Hz, 4H, O—CH$_2$—CH$_2$).

(3)

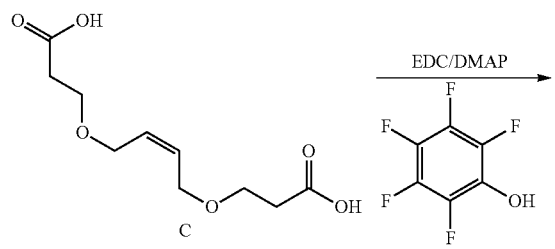

which was dissolved in CH$_2$Cl$_2$. 1.1 eq of N-(tert-butoxycarbonyl)ethanolamine (5.32 g, 33 mmol) and 10 mol % 4-dimethylaminopyridine (DMAP) were added. After stirring over night, the solution was concentrated. Ether was added to precipitate DMAP salt, and the solution was filtered. This step was repeated until no more DMAP salts precipitated and the pure zwitterion was obtained. The isolated yield was 60-70%.

$^1$H-NMR (300 MHz, CDCl$_3$): δ=1.41 (s, 9H, H9), 2.83 (m, 2H, H3 & H3'), 3.37 (m, 2H, H6), 4.18 (m, 2H, H5), 5.24 & 5.32 (s, 2H, H2 & H2'), 6.46 (m, 2H, H1 & H1'), 7.5-8.2 (br s, 1H, OH). HR-MS (FAB): calc. 299.31 g/mol. found 272.1 g/mol (M-t-Butyl).

The diamine monomer 3

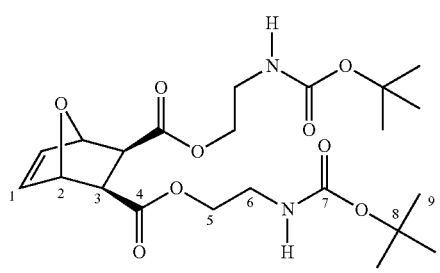

was obtained in a one pot-synthesis from exo-7-oxabicyclo[2.2.1]hept-5-ene-2,3-dicarboxylic acid anhydride 1 (see above) without isolating the intermediate 2:1 (5 g, 30.0 mmol) was dissolved in CH$_2$Cl$_2$. 1.1 eq of N-(tert-butoxycarbonyl)ethanolamine (5.32 g, 33 mmol) and 10 mol % 4-dimethylaminopyridine (DMAP) were added. After stirring over night at room temperature, the solution was cooled to 0° C. 1.1 eq N-(tert-butoxycarbonyl)ethanolamine (5.32 g, 33 mmol) and 1.0 eq (6.19 g, 30 mmol) DCC(N,N'-dicyclohexylcarbodiimide) were added, and the mixture was stirred over night. The precipitate was filtered through a short alumina column (5 cm neutral Al$_2$O$_3$/dichlormethane) and a clear solution was obtained. The solvent was removed by vacuum evaporation and the crude product was chromatographed (15 cm silica gel, hexane:ethyl acetate gradient, 9:1 to 1:1). Evaporation of the solvent yielded the pure monomer. The isolated yield was 70 to 80%.

$^1$H-NMR (300 MHz, CDCl$_3$): d=1.41 (s, 18H, H9), 2.81 (s, 2H, H3), 3.36 (m, 4H, H6), 4.17 (m, 4H, H5), 5.25 (s, 2H, H2), 6.44 (s, 2H, H1). $^{13}$C-NMR (75 MHz, CDCl$_3$): d=28.39 (C9), 39.44 (C6), 47.03 (C3), 64.79 (C5), 80.55 (C2), 136.66 (C1), HR-MS (FAB): calc. 470.52 g/mol. found 471.23 g/mol.

contrast to the preparation of low molecular weight oligomers as shown in the prior art (see above), the order of reagent addition was reversed, and Grubbs 3$^{rd}$ generation catalyst with pyridine as ligands (G3') was used instead of the traditional G3 with 2-bromo pyridine ligands (see above preparation of a variation of Grubbs 3$^{rd}$ generation catalyst). In a typical experiment, 500 mg monomer and the respective amount of G3' (see Table 1 for details) were dissolved in 4 and 1 mL dichloromethane, respectively, and subject to three freeze-thaw cycles. The monomer was added in one shot to the vigorously stirring catalyst solution at room temperature under argon. After 30 min, the polymer chain was end-capped with an excess of ethylvinyl ether (1 mL). The solution was allowed to stir over night. After evaporation of the solvent and drying, an aliquot of each polymer was taken for GPC and NMR analysis. The product was a brownish solid.

R=Ethyl: 1H-NMR (300 MHz, CDCl$_3$): 1.24 (s, 3H, CH$_2$—CH$_3$), 1.42 (s, 9H, H9), 3.09 (br m, 2H, H3 & H3'), 3.34 (br m, 2H, H6), 4.16 (br m, 4H, CH$_2$—CH$_3$ and H5), 4.72 (br m, 1H, H2 & H2' trans), 5.10 (br m, 1H, H2 & H2' cis), 5.30 (br s, 1H, NH), 5.58 (br m, 1H, H1 & H1' cis), 5.88 (br m, 1H, H1 & H1' trans).

R=Propyl: 1H-NMR (300 MHz, CDCl$_3$): 0.92 (m, 3H, CH2-CH3), 1.43 (s, 9H, H9), 1.62 (m, 2H, β-CH$_2$), 3.12 (br in, 2H, H3 & H3'), 3.34 (br m, 2H, H6), 4.10 (m, 4H, α-CH$_2$ and H5), 4.69 (br in, 1H, H2 & H2' trans), 5.12 (br m, 1H, H2 cis & H2'), 5.31 (br m, 1H, H1 & H1' cis), 5.59 (br s, 1H, NH), 5.88 (br m, 1H, H1 & H1' trans).

R=Butyl: 1H-NMR (300 MHz, CDCl$_3$): 0.87 (m, 3H, CH2-CH3), 1.29 (m, 2H, γ-CH2), 1.43 (s, 9H, H9), 1.59 (m, 2H, β-CH2), 3.11 (br m, 2H, H3 & H3'), 3.37 (br m, 2H, H6), 4.10 (m, 4H, α-CH2 and H5), 4.73 (br m, 1H, H2 & H2' trans), 5.11 (br m, 1H, H2 & H2' cis), 5.35 (br s, 1H, NH), 5.59 (br m, 11-1, H1 & H1' cis), 5.88 (br m, 1H, H1 & H1' trans).

The signals of the propyl-diamine and the butyl-diamine copolymers correspond to an overlay of the respective homopolymers.

Diamine homopolymer: 1H-NMR (300 MHz, CDCl$_3$): 1.42 (s, 9H, H9), 3.15 (br m, 2H, H3), 3.36 (br m, 2H, H6), 4.16 (br m, 2H, H5), 4.72 (m, 1H, H2 trans), 5.10 (br s, 1H, H2 cis), 5.42 (br s, 1H, NH), 5.60 (br m, 1H, H1 cis) and 5.89 (br m, 1H, H1 trans).

TABLE 1

Experimental parameters for polymer synthesis

| Sample | Monomer | N$_{repeat\ units}$ | M$_{n\ Target}$ g mol$^{-1}$ | M$_{Monomer}$ g mol$^{-1}$ | n$_{Monomer}$ mmol | m$_{Monomer}$ mg | M$_{Catalyst}$ g mol$^{-1}$ | n$_{Catalyst}$ mmol | m$_{Catalyst}$ mg |
|---|---|---|---|---|---|---|---|---|---|
| Ethyl_500k | Ethyl | 1408 | 500000 | 355 | 1.41 | 500 | 727 | 0.001 | 0.73 |
| Propyl_500k | Propyl | 1355 | 500000 | 369 | 1.36 | 500 | 727 | 0.001 | 0.73 |
| Butyl_500k | Butyl | 1305 | 500000 | 383 | 1.31 | 500 | 727 | 0.001 | 0.73 |
| P_A_500k | Propyl Diamine | | 500000 | 369 471 | | | 727 | 0.001 | 0.73 |
| B_A_500k | Butyl Diamine | | 500000 | 485 471 | | | 727 | 0.001 | 0.73 |

5—Homopolymerization:

High molecular weight ROMP polymers were synthesized using monomers as described herein (polymers based on single use of monomers with R=ethyl, propyl, butyl, all with a 2-aminoethyl moiety as a hydrophilic component, or polymers as mixed polymers based on single use of monomers with (one) R=propyl or butyl, preferably with one 2-aminoethyl moiety, and monomers with two 2-aminoethyl moieties (Diamine), i.e. two hydrophilic components instead of one hydrophilic component and one hydrophobic component). In 6—Crosslinker Synthesis (=BP-Silane)

The triethoxysilane benzophenone crosslinker has been synthesized as reported previously (see M. Gianneli, R. F. Roskamp, U. Jonas, B. Loppinet, G. Fytas, W. Knoll, Soft Matter 2008, 4, 1443-1447). In short, 4-Allyloxybenzophenone was dissolved in 10 fold excess of triethoxysilane at room temperature under nitrogen. 10 mol % activated Pt—C was added. The solution was stirred at room temperature until thin layer chromatography indicated that the 4-allyloxybenzophenone had been consumed (typically 2 days). The catalyst was removed by filtration. Excess triethoxysilane was removed by evaporation. The crude product was dissolved in ethanol to yield a 50 mM solution and was used without further purification. Spectroscopic data was identical to those described in M. Gianneli et al. (2008, supra).

7—Surface Preparation and Binding for "Photo-Crosslinking" Approach

The surface for immobilizing the inventive antimicrobial polymer was prepared as follows:

1. Clean silicon wafers (12 cm diameter) were rinsed with toluene and dried under $N_2$. 2 mL of BP-Silane was filtered through a 0.45 µm syringe filter and added dropwise to the center of the wafer. It was then spincoated at 500-1000 rpm for 60 sec. The silicon wafer was immediately placed on a hot plate at 100° C. and baked for 30 min. It was then further rinsed with toluene, isopropanol and ethanol, and dried under nitrogen.
2. 50 mg of the inventive antimicrobial polymer was wetted with 0.5 ml dichloromethane and allowed to swell for 15 min. Then, 4.5 ml of toluene were added, yielding a 10 mg $mL^{-1}$ solution. 1.5 mL of polymer solution was filtered through a 0.45 µm syringe filter and added dropwise to the center of the silanized silicon wafer. It was then spincoated at 500-1000 rpm for 60 sec, yielding a 30-60 nm thick polymer film.
3. The inventive antimicrobial polymer-coated silicon wafer was covalently crosslinked at a wavelength of 250 nm for 30 min using a Strata-linker device (Stratagene). The coated silicon wafer was then rinsed with toluene (2×) and dichloromethane (2×) to remove the excess polymer, and dried under $N_2$.
4. The polymer-coated silicon wafer was immersed into a 4 M solution of HCl in dioxane over night. It was the rinsed with isopropanol and ethanol (2×) to remove reaction byproducts, and subject to further characterization.

8—Surface Preparation and Binding for "Grafting onto" Surfaces

For coating the surface with an inventive antimicrobial polymer via grafting onto a surface was pretreated to comprise oxide or hydroxide groups; the surface was then functionalized by covalently binding a reactive silane compound to the pretreated surface. The inventive end-functionalized (protected) antimicrobial polymer as prepared herein was then bound to the reactive silane compound of the functionalized surface, thereby covalently binding the inventive end-functionalized antimicrobial polymer to the surface. Subsequently, a post-"grafting onto" treatment of the covalently bound inventive antimicrobial polymer was carried out by deprotection the inventive polymers with TFA and washing the coated polymer carrying out washing steps.

9—Surface Preparation and Binding for "Grafting from" Surfaces

For coating the surface with an inventive antimicrobial polymer via grafting from an alkenyl-functionalized silicon wafer was immersed into a 5 mM solution of Grubbs $2^{nd}$ generation catalyst in dichlormethane under argon for 10 min. It was then thoroughly rinsed. This was followed by an immersion of the wafer into a 0.05 mM solution of propyl monomer in dichloromethane. After 10 min, 1 mL of ethylvinyl ether was added to quench the polymerization reaction. The wafer was then Soxlett extracted with dichloromethane over night and deprotected with HCl to yield the active antimicrobial polymer.

10—Determination of the Antimicrobial Activity of the Inventive Antimicrobial Polymers when Covalently Bound to a Silicon Wafer Experimental Setup Inventive antimicrobial polymers (R=propyl, M=500,000 g $mol^{-1}$) were covalently bound to a silicon wafer as described herein. The thickness of the layer of the inventive antimicrobial polymers was found to be 20 nm as determined via ellipsometric analysis. Atomic force microscopy revealed a coarseness or roughness of about 8.4 nm (see FIG. 1).

Subsequently, a bacterial culture from *Enterococcus faecalis* was prepared over night. Starting from this culture a bacterial suspension from *Enterococcus faecalis* was prepared containing $10^6$ CFU/ml in PBS. To allow determination of the antimicrobial activity of the modified silicon wafer the materials to be tested for initial adhesion were incubated for 2 hours in the bacterial solution.

Prior to this, the materials were embedded into silicon in a 24 well plate with their uncoated side. In this context, uncoated materials served as a negative control, and materials coated with chlorohexidin served as a positive control. Prior to incubation the materials were disinfected with 70% isopropanol, the excess isopropanol was pipetted off and dried in a drying chamber at 37° C. The number of surviving initial adherent microorganisms was determined via CFU (Müller-Hinton-Agar) and Live/Dead-staining. In order to exclude diffusion of active components from the antimicrobially coated surfaces a material sample of the same batch was laid on a plate with Müller-Hinton-Agar. In parallel, a positive control was laid on the same plate with Müller-Hinton-Agar. The live/dead staining was carried out using the "LIVE/DEAD BacLight™ Bacterial Viability Kit" (Molecular Probes, Inc. Oregon, USA) according to the manufacturer's instructions. Analysis and picture digitalizing were carried out using an epifluorescence microscope (Zeiss, Oberkochen, Germany). The number of adherent bacteria (CFU) was calculated in $cm^2$.

Results

It could be shown that covalently binding the inventive antimicrobial polymers to the modified silicon wafer led to a significant reduction of pathogens cultured from *Enterococcus faecalis* of at least two steps in the logarithmic scale (see FIG. 2). The standard deviation was influenced by flocculation caused by *Enterococcus faecalis*. Flocculation was removed by ultrasound treatment, which led to a slight variation of the number of CFUs.

The treated modified silicon wafer was subjected to a live/dead staining. The live/dead staining showed a higher number of non vital cells (dead cells) from *Enterococcus faecalis* stained with propidium iodide (living cells) (see FIG. 3, upper row), when compared to vital cells stained with systo 9 (see FIG. 3, lower row).

11—Determination of Thickness from Ellipsometry/nm

As described previously by Prucker et al. (J. Am. Chem. Soc. 1999, 121, 8766) for polystyrene, a molecular weight of 50 000 g/mol is necessary to achieve complete coverage of a surface using the benzophenone method. For the inventively used polynorbornene polymers, the present inventors surprisingly found that a molecular weight of higher than 100,000 g/mol and even more preferably of higher than 250 000 g/mol is particularly advantageous to obtain a film that is covalently attached to the surface. The present inventors showed this by ellipsometry in the following control experiment: Si wafers were plasma cleaned and silanized with BP-Silane as described in example 7, step 1-3. Polymer solutions from KL004, KL009, KL010 and KL011 were used. The resulting polymer-covered wafers were washed with dichloromethane after UV irradiation. The results from ellipsometry are shown below. This data shows that particularly the SMAMP with a molecular weight of 500 000 g/mol formed a covalently attached film on the surface. The reason for this is the statistical nature of cross-linking with UV-activated species. For the successful formation of a covalent bond, the radical species formed on the benzophenone linker molecule must be close enough to a polymer segment of the polymer chain. For a polymer with low molecular weight, the probability to form a sufficient number of covalent bonds to the silanized wafer is thus very low. Therefore, only high molecular weight polymers weight of higher than 100,000 g/mol and even more preferably of higher than 250 000 g/mol can be used to form such coatings.

| Sample | Thickness from Ellipsometry/nm |
|---|---|
| Benzophenone silane | 2.2 |
| SMAMP 3000 g/mol (KL004) | 2.3 |
| SMAMP 50 000 g/mol (KL008) | 2.2 |
| SMAMP 100 000 g/mol (KL009) | 2.3 |
| SMAMP 250 000 g/mol (KL010) | 2.3 |
| SMAMP 500 000 g/mol (KL011) | 20.4 |

The invention claimed is:

1. Substrate comprising an antimicrobial polymer covalently bound to a surface of the substrate, the antimicrobial polymer comprising a number average molecular weight ($M_n$) of more than 100,000 g mol$^{-1}$ and as a repeat unit a structure according to formula (I):

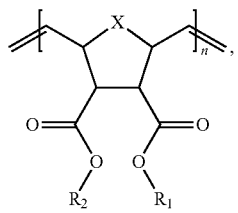

wherein one of moieties $R_1$ and $R_2$ comprises a hydrophobic group and the other one of moieties $R_1$ and $R_2$ comprises a hydrophilic group,
wherein X is O, S or $CR_3R_4$, wherein $R_3$ and $R_4$ are independently from each other selected from a hydrogen or a $C_1$-$C_{12}$ alkyl or alkoxy group, and
n is an integer selected from about 250 to about 2500.

2. Substrate according to claim 1, wherein the hydrophobic group is selected from linear, branched, cyclic, substituted and unsubstituted, saturated, partially saturated and/or unsaturated ($C_1$-$C_{30}$) alkyl, ($C_1$-$C_{30}$) alkenyl, ($C_1$-$C_{30}$) alkynyl, or ($C_1$-$C_{30}$) aryl groups, ($C_1$-$C_{30}$) heteroalkyl, ($C_1$-$C_{30}$) heteroalkenyl, ($C_1$-$C_{30}$) heteroalkynyl, ($C_1$-$C_{30}$) heteroaryl, or ($C_1$-$C_{30}$) heteroarylalkyl groups, or from linear, branched, cyclic, substituted, unsubstituted, saturated, partially saturated and/or unsaturated ($C_1$-$C_{30}$) cycloalkyl, ($C_1$-$C_{30}$) cycloalkenyl, ($C_1$-$C_{30}$) cycloalkynyl, ($C_1$-$C_{30}$) heterocycloalkyl, and ($C_1$-$C_{30}$) heterocycloalkenyl-groups.

3. Substrate according to claim 1, wherein the hydrophobic group of $R_1$ or $R_2$ is selected from the group

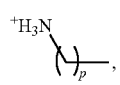

wherein p is an integer selected from 1-10.

4. Substrate according to claim 1, wherein the hydrophilic group is selected from hydroxyl, methoxy, phenyl, carboxylic acids and ions and salts thereof, methyl, ethyl, and vinyl esters of carboxylic acids, amides, amino, cyano, isocyano, nitrile, ammonium ions or salts, sulfonium ions or salts, phosphonium ions or salts, mono- and di-alkyl substituted amino groups, polypropyleneglycols, polyethylene glycols, glycosyl groups, sugars, epoxy groups, aerylates, sulfonamides, nitro, $OP(O)(OCH_2CH_2N^+RRR)O^-$ guanidinium, aminate, acrylamide, pyridinium, piperidine, and combinations thereof, wherein each R is independently selected from H or alkyl, from polymethylene chains substituted with alcohol, carboxylate, acrylate, or methacrylate, or from alkyl chains having internal amino or substituted amino groups, including internal —NH, —NC(O)R, or —NC(O)CH=$CH_2$-groups, wherein R is H or alkyl, from polycaprolactone(s), polycaprolactone diol(s), poly(acetic acid)(s), poly(vinyl acetates)(s), poly(2-vinyl pyridine)(s), cellulose ester(s), cellulose hydroxylether(s), poly(L-lysine hydrobromide)(s), poly(itaconic acid)(s), poly(maleic acid)(s), poly(styrenesulfonic acid)(s), poly(aniline)(s), or poly(vinyl phosphonic acid)(s).

5. Substrate according to claim 1, wherein the hydrophilic group of $R_1$ or $R_2$ is selected from ammonium ions, sulfonium ions, phosphonium ions, and mono- and di-alkyl substituted amino groups, from an $C_1$-$C_{12}$ alkyl comprising a group selected from ammonium ions, sulfonium ions, phosphonium ions, and mono- and di-alkyl substituted amino groups.

6. Substrate according to claim 1, wherein X is O, $R_1$ is a linear or branched $C_1$-$C_{12}$ alkyl group as defined above, and $R_2$ is

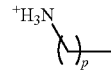

wherein p is an integer selected from 1-10.

7. Substrate according to claim 1, wherein X is $CR_3R_4$, wherein $R_3$ and $R_4$ are independently from each other selected from a hydrogen, or a $C_1$-$C_{12}$ alkyl or alkoxy group; and $R_1$ is a linear or branched $C_1$-$C_{12}$ alkyl group; and $R_2$ is

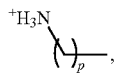

wherein p is an integer selected from 1-10.

8. Substrate according to claim 1, wherein the polymer according to formula (I) is a co-polymer comprising as repeat units a structure according to formula (I') and a further structure according to formula (I"):

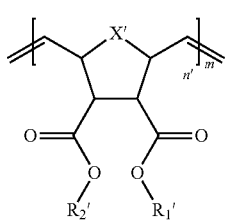

and

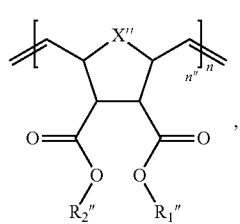

(I')

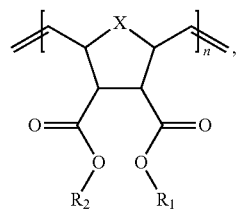

(I)

wherein each of X' and X" in formulae (I') and (I") is independent from each other O, S or $CR_3R_4$, wherein $R_3$ and $R_4$ are independently from each other selected from a hydrogen or a $C_1$-$C_{12}$ alkyl or alkoxy group; each of $R_1'$ and $R_1''$ is a hydrophobic group and each of $R_2'$ and $R_2''$ is a hydrophilic group, provided that $R_1'$ and $R_1''$ are not the same, $R_2'$ and $R_2''$ are the same, or X' and X" are not the same; and each of n' and n" is an integer selected from about 250 to about 2500, wherein n'+n"=n.

9. Substrate according to claim 1, wherein the covalent binding of the antimicrobial polymer to the surface is carried out via photoactivation, via a photoreactive crosslinker, or via a "grafting from" or a "grafting onto" technique.

10. Substrate according to claim 1, wherein the antimicrobial polymer is applied to the surface of the substrate via spin-coating or dip-coating.

11. Substrate according to claim 1, wherein the surface of the substrate is selected from an inorganic surface containing or comprising metals or alloys, iron, gold, silver, copper, aluminum, nickel, chrome, titanium, molybdenum, magnesium, zirconium, ceramics, titanium oxides, or zirconium oxides.

12. Substrate according to claim 1, wherein the substrate is selected from any implant, dental implant, prosthesis, joint, bone, tooth, artificial joint, artificial bone, artificial tooth, inlays, or a material used or to be used for implanting such a substrate, screws, anchors, fastener or fixing material, a medical or surgical device or tool, any wound dressing material, bed sheets for clinical or medical purposes, sheets for covering medical devices, bindings or book covers, keyboards, computer keyboards, computer, laptops, displays, display covers, lamps, grips of tools and instruments, biomaterial suitable for tissue support, from a cell or tissue carrier system, biomaterial for volume preservation of solid body tissues, or from surfaces or substrates used for storage of cells, tissue, organs, or for storage of food, of refrigerators, coolers, or storage boxes.

13. Method for antimicrobially coating a surface or a substrate comprising the steps:
providing an antimicrobial polymer as defined according to claim 1, and
binding the antimicrobial polymer covalently to the surface or substrate.

14. Method for antimicrobially coating a surface or a substrate comprising the steps:
providing an antimicrobial polymer covalently bound to a surface of a substrate, the antimicrobial polymer comprising a number average molecular weight ($M_n$) of more than 100,000 g mol$^{-1}$ and as a repeat unit a structure according to formula (I):

wherein one of moieties $R_1$ and $R_2$ comprises a hydrophobic group and the other one of moieties $R_1$ and $R_2$ comprises a hydrophilic group,
wherein X is O, S or $CR_3R_4$, wherein $R_3$ and $R_4$ are independently from each other selected from a hydrogen or a $C_1$-$C_{12}$ alkyl or alkoxy group, and
n is an integer selected from about 250 to about 2500,
binding the antimicrobial polymer covalently to the surface or a substrate, wherein the surface of the substrate is selected from an inorganic surface containing or comprising metals or alloys, iron, gold, silver, copper, aluminum, nickel, chrome, titanium, molybdenum, magnesium, zirconium, ceramics, titanium oxides, or zirconium oxides, wherein the substrate is selected from any implant, dental implant, prosthesis, joint, bone, tooth, artificial joint, artificial bone, artificial tooth, inlays, or a material used or to be used for implanting such a substrate, screws, anchors, fastener or fixing material, from a medical or surgical device or tool, including implant trephine or trepan drill, scalpels, forceps, scissors, screws, fasteners and/or fixing material used for implantation, holders, clips, clamps, needles, linings, tubes, water tubes, pipes, water pipes, bottles and bottle inlays, inlays for medical equipment, (surfaces of) operating tables, treatment chairs, catheter, stents, any wound dressing material, including plaster, gauzes, bandages, bed sheets for clinical or medical purposes, sheets for covering medical devices, bindings or book covers, keyboards, computer keyboards, computer, laptops, displays, display covers, lamps, grips of tools and instruments, biomaterial suitable for tissue support, from a cell or issue carrier system, biomaterial suitable for volume preservation of solid body tissues, or from surfaces or substrates used for storage of cells, tissue, organs, or for storage of food, of refrigerators, coolers, or storage boxes.

15. Substrate according to claim 12, wherein the medical or surgical device or tool includes at least one of implant trephine or trepan drill, scalpels, forceps, scissors, screws, fasteners and/or fixing material used for implantation, holders, clips, clamps, needles, linings, tubes, water tubes, pipes, water pipes, bottles and bottle inlays, inlays for medical equipment, (surfaces of) operating tables, treatment chairs, catheter, and stents.

16. Substrate according to claim 12, wherein the wound dressing material includes at least one of plaster, gauzes, and bandages.

* * * * *